(12) United States Patent
Lee

(10) Patent No.: US 8,740,982 B2
(45) Date of Patent: Jun. 3, 2014

(54) DEVICES CONTAINING A CHEMONUCLEOLYSIS AGENT AND METHODS FOR TREATING AN INTERVERTEBRAL DISC OR SPINAL ARACHNOIDITIS

(75) Inventor: Elaine Lee, Santa Clara, CA (US)

(73) Assignee: Kyphon Sarl, Neuchatel (CH)

( * ) Notice: Subject to any disclaimer, the term of this patent is extended or adjusted under 35 U.S.C. 154(b) by 80 days.

(21) Appl. No.: 12/911,981

(22) Filed: Oct. 26, 2010

(65) Prior Publication Data
US 2012/0101578 A1 Apr. 26, 2012

(51) Int. Cl.
*A61F 2/44* (2006.01)
(52) U.S. Cl.
USPC .................................................. 623/17.16
(58) Field of Classification Search
USPC ............................................ 623/17.11–17.16
See application file for complete search history.

(56) References Cited

U.S. PATENT DOCUMENTS

| | | | |
|---|---|---|---|
| 4,624,255 A | 11/1986 | Schenck et al. | |
| 4,863,457 A | 9/1989 | Lee | |
| 4,938,763 A * | 7/1990 | Dunn et al. ............... | 604/891.1 |
| 5,522,844 A | 6/1996 | Johnson | |
| 5,626,838 A | 5/1997 | Cavanaugh, Jr. | |
| 5,759,583 A | 6/1998 | Iwamoto et al. | |
| 5,868,789 A | 2/1999 | Huebner | |
| 5,942,241 A | 8/1999 | Chasin et al. | |
| 6,069,129 A | 5/2000 | Sandberg et al. | |
| 6,179,862 B1 | 1/2001 | Sawhney | |
| 6,248,345 B1 | 6/2001 | Goldenheim et al. | |
| 6,287,588 B1 | 9/2001 | Shih et al. | |
| 6,326,020 B1 | 12/2001 | Kohane et al. | |
| 6,331,311 B1 | 12/2001 | Brodbeck et al. | |
| 6,428,804 B1 | 8/2002 | Suzuki et al. | |
| 6,451,335 B1 * | 9/2002 | Goldenheim et al. ........ | 424/426 |
| 6,461,631 B1 | 10/2002 | Dunn et al. | |
| 6,524,607 B1 | 2/2003 | Goldenheim et al. | |
| 6,534,081 B2 | 3/2003 | Goldenheim et al. | |
| 6,589,549 B2 | 7/2003 | Shih et al. | |

(Continued)

FOREIGN PATENT DOCUMENTS

WO 2009111066 A1 9/2009

OTHER PUBLICATIONS

D. Ewen Cameron M. D., L. Levy M. D. and W. Hunzinger M.D.1 "Intrathecal Administration of Hyaluronidase: Effects Upon the Behavior of Patients Suffering From Senile and Arteriosclerotic Behavior Disorders", Am J Psychiatry 113:893-900, Apr. 1957 doi: 10.1176/appi.ajp.113.10.893, 1 The Allan Memorial Institute of Psychiatry, 1025 Pine Avenue West, Montreal, Canada. 1 pg.

(Continued)

*Primary Examiner* — Mary Hoffman
(74) *Attorney, Agent, or Firm* — Sorell Lenna & Schmidt LLP

(57) ABSTRACT

Effective devices and methods using a chemonucleolysis agent are provided for treating an intervertebral disc or treating spinal arachnoiditis. The devices and methods comprise a chemonucleolysis agent to degrade or to shrink at least a portion of the intervertebral disc. In some embodiments, the methods and devices are configured to immediately release an effective amount of the chemonucleolysis agent within 24 hours and provide sustained release of the chemonucleolysis agent over a period of up to one year to treat the intervertebral disc. In some embodiments, the chemonucleolysis agent in the device is administered in or near the intrathecal space and/or thecal sac to treat spinal arachnoiditis.

12 Claims, 3 Drawing Sheets

(56) References Cited

U.S. PATENT DOCUMENTS

| | | | |
|---|---|---|---|
| 6,630,155 | B1 | 10/2003 | Chandrashekar et al. |
| 6,632,457 | B1 | 10/2003 | Sawhney |
| 6,756,058 | B2 | 6/2004 | Brubaker et al. |
| 6,773,714 | B2 | 8/2004 | Dunn et al. |
| 6,921,541 | B2 | 7/2005 | Chasin et al. |
| 6,958,149 | B2 | 10/2005 | Vukicevic et al. |
| 6,974,462 | B2 | 12/2005 | Sater |
| 7,132,098 | B2 * | 11/2006 | Masuda et al. ............. 424/94.61 |
| 7,144,412 | B2 | 12/2006 | Wolf et al. |
| 7,166,570 | B2 | 1/2007 | Hunter et al. |
| 7,220,281 | B2 | 5/2007 | Lambrecht et al. |
| 7,229,441 | B2 | 6/2007 | Trieu et al. |
| 7,235,043 | B2 | 6/2007 | Gellman et al. |
| 7,287,983 | B2 | 10/2007 | Ilan |
| 7,318,840 | B2 | 1/2008 | McKay |
| 7,329,259 | B2 | 2/2008 | Cragg |
| 7,361,168 | B2 | 4/2008 | Makower et al. |
| 7,367,978 | B2 | 5/2008 | Drewry et al. |
| 7,572,440 | B2 | 8/2009 | Vukicevic et al. |
| 2002/0009454 | A1 | 1/2002 | Boone et al. |
| 2002/0090398 | A1 | 7/2002 | Dunn et al. |
| 2003/0185873 | A1 | 10/2003 | Chasin et al. |
| 2003/0204191 | A1 | 10/2003 | Sater et al. |
| 2003/0224033 | A1 | 12/2003 | Li et al. |
| 2004/0072799 | A1 | 4/2004 | Li et al. |
| 2004/0082540 | A1 | 4/2004 | Hermida Ochoa |
| 2004/0109893 | A1 | 6/2004 | Chen et al. |
| 2004/0214793 | A1 | 10/2004 | Hermida Ochoa |
| 2004/0268425 | A1 | 12/2004 | Bookbinder et al. |
| 2005/0142163 | A1 | 6/2005 | Hunter et al. |
| 2005/0175709 | A1 | 8/2005 | Baty, III et al. |
| 2005/0186261 | A1 | 8/2005 | Avelar et al. |
| 2005/0197293 | A1 | 9/2005 | Mellis et al. |
| 2006/0074422 | A1 | 4/2006 | Story et al. |
| 2006/0106361 | A1 | 5/2006 | Muni et al. |
| 2006/0148903 | A1 | 7/2006 | Burch et al. |
| 2006/0183786 | A1 | 8/2006 | Wang |
| 2006/0189944 | A1 | 8/2006 | Campbell et al. |
| 2006/0228391 | A1 | 10/2006 | Seyedin et al. |
| 2007/0128575 | A1 * | 6/2007 | Trieu ............................ 433/25 |
| 2007/0156180 | A1 | 7/2007 | Jaax et al. |
| 2007/0185497 | A1 | 8/2007 | Cauthen et al. |
| 2007/0202074 | A1 | 8/2007 | Shalaby |
| 2007/0243225 | A1 | 10/2007 | McKay |
| 2007/0243228 | A1 | 10/2007 | McKay |
| 2007/0248639 | A1 | 10/2007 | Demopulos et al. |
| 2007/0253994 | A1 | 11/2007 | Hildebrand |
| 2007/0258941 | A1 * | 11/2007 | Pfister ........................ 424/78.27 |
| 2008/0091207 | A1 | 4/2008 | Truckai et al. |
| 2009/0214505 | A1 | 8/2009 | Bookbinder et al. |
| 2010/0003237 | A1 | 1/2010 | Keller et al. |
| 2010/0003238 | A1 | 1/2010 | Frost et al. |

OTHER PUBLICATIONS

Fernández Cañabate E., Longoni Merino M., Garriga Biosca R., Navas Vinagre I. "Administration of intrathecal hyaluronidase in a patient diagnosed with adhesive arachnoiditis" Farm Hosp. Jan.-Feb. 2008;32(1):58-60. Spanish. No abstract available. PMID: 18426706 [PubMed—indexed for MEDLINE] Free Article Related citations. 3 pgs.

Gourie-Devi M, Satishchandra P., "Hyaluronidase as an adjuvant in the management of tuberculous spinal arachnoiditis". J Neurol Sci. Mar. 1991;102(1):105-11.PMID: 1856727 [PubMed—indexed for MEDLINE] Related citations, 1 pg.

Gourie-Devi M, Satish P., "Intrathecal hyaluronidase treatment of chronic spinal arachnoiditis of noninfective etiology". Surg Neurol. Sep. 1984;22(3):231-4.PMID: 6547785 [PubMed—indexed for MEDLINE] Related citations, 1 pg.

Gegalian L., "Use of hyaluronidase in the central nervous system." Surg Neurol. Jul. 1979;12(1):3-5.PMID: 451858 [PubMed—indexed for MEDLINE] Related citations, 1 pg.

Gleeson, Pauls, "Obstetrical Physical Therapy", Physical Therapy, vol. 681 / No. 11, Nov. 1988, 4 pgs.

Siegal, Rengachary, "Carpal Tunnel Symdrome in Pregnancy", Thieme 1996, Neurosurgical aspects of pregnancy, Issue 494, 5 pgs.

Whitesell, London, "Neuromuscular complications of pregnancy", Medlink 2008, 7 pgs.

AMA CSA, "Effects of work on pregnancy", 1999, 19 pgs.

Rose, "Carpal Tunnel Syndrome relieved by pregnancy", British Medical Journal, Mar. 31, 1956, 744-745, 2 pgs.

Bjorkqvist, Lang, Punnonen, Rauramo, "Carpal Tunnel syndrome in ovariectomized women.", AOGS 1977, 56(2):127-30., abstract, 1 pg.

Dekel, Papaionnou, Rushworth, Coates, "Idiopathic carpal tunnel syndrome caused by carpal stenosis", British Medical Journal, May 31, 1980, 3 pgs.

Samuel, "Relaxin: Antifibrotic Properties and Effects in Models of Disease", Clinical Medicine & Res., vol. 3, No. 4: 241-249, 2005, 9 pgs.

Halozyme Therapeutics, "Product Pipeline", 2010, 2 pgs.

* cited by examiner

DEVICES CONTAINING A CHEMONUCLEOLYSIS AGENT AND METHODS FOR TREATING AN INTERVERTEBRAL DISC OR SPINAL ARACHNOIDITIS

BACKGROUND

In human anatomy, the spine is a generally flexible column that can take tensile and compressive loads. The spine also allows bending motion and provides a place of attachment for muscles and ligaments. Generally, the spine is divided into three sections: the cervical spine, the thoracic spine and the lumbar spine. The sections of the spine are made up of individual bones called vertebrae. Also, the vertebrae are separated by intervertebral discs, which are situated between adjacent vertebrae.

The intervertebral discs function as shock absorbers and as joints. Further, the intervertebral discs can absorb the compressive and tensile loads to which the spinal column may be subjected. At the same time, the intervertebral discs can allow adjacent vertebral bodies to move relative to each other a limited amount, particularly during bending, or flexure, and torsion of the spine. Thus, the intervertebral discs are under constant muscular and/or gravitational pressure and generally, the intervertebral discs are the first parts of the lumbar spine to show signs of deterioration.

The intervertebral disc functions to stabilize the spine and to distribute forces between vertebral bodies. The intervertebral disc is composed of three structures: the nucleus pulposus, the annulus fibrosis, and two vertebral end plates. These components work to absorb the shock, stress, and motion imparted to the human vertebrae. The nucleus pulposus is an amorphous hydrogel containing proteoglycans with the capacity to bind water. The nucleus pulposus is maintained within the center of an intervertebral disc by the annulus fibrosis, which is composed of highly structured collagen fibers. The vertebral end plates, composed of hyaline cartilage, separate the disc from adjacent vertebral bodies and act as a transition zone between the hard vertebral bodies and the soft disc.

Intervertebral discs may be displaced or damaged due to trauma or disease. Disruption of the annulus fibrosis may allow the nucleus pulposus to protrude into the vertebral canal, a condition commonly referred to as a herniated or ruptured disc. The extruded nucleus pulposus may press on a spinal nerve, which may result in nerve damage, back pain, numbness, muscle weakness, sciatica, spinal arachnoiditis, and, in severe cases, paralysis. Intervertebral discs may also deteriorate due to the normal aging process. As a disc dehydrates and hardens, the disc space height will be reduced, leading to instability of the spine, decreased mobility and back pain.

One way to relieve the symptoms of these conditions is by surgical removal of a portion or the entire intervertebral disc. The removal of the damaged or unhealthy disc may allow the disc space to collapse, which would lead to instability of the spine, abnormal joint mechanics, nerve damage, as well as severe back pain. Therefore, after removal of the disc, adjacent vertebrae are typically fused to preserve the disc space. Spinal fusion involves inflexibly connecting adjacent vertebrae through the use of bone grafts or metals rods. Because the fused adjacent vertebrae are prevented from moving relative to one another, the vertebrae no longer rub against each other in the area of the damaged intervertebral disc and the likelihood of continued pain and inflammation is reduced. Spinal fusion, however, is disadvantageous because it restricts the patient's mobility by reducing the spine's flexibility, and it is a relatively invasive procedure.

Attempts to overcome these problems have led researchers to investigate the efficacy of implanting an artificial intervertebral disc to replace, completely or partially, the patient's damaged intervertebral disc. Disc replacement surgery generally involves removing the disc or damaged portion thereof and placement of an artificial disc in the evacuated disc space. Some desirable attributes of a hypothetical implantable disc include axial compressibility for shock absorbance, excellent durability to avoid future replacement, minimally invasive placement of the artificial disc to reduce post-operative discomfort, and biocompatibility. Existing artificial intervertebral discs include, for example, mechanically based (e.g. comprising rotational surfaces or springs), polymer based, and biopolymer based artificial discs.

Other attempts have focused on restoring disc height in, for example, a dehydrated intervertebral disc, where a portion or all of the nucleus pulposus and a prosthetic nucleus device is implanted in the intervertebral disc space to augment or completely replace the dehydrated nucleus. These types of procedure where all or a portion of the nucleus pulposus is augmented is frequently referred to as "disc augmentation".

Sometimes, a total disc replacement operation may be performed where not just the dehydrated nucleus but the entire intervertebral disc is removed and replaced with a prosthesis. However, these types of treatment often involve complex surgery, many invasive and traumatic entries at, near, or in the intervertebral disc that inflict a good deal of trauma on the patient, resulting in increased post-surgical recovery times and disability.

Spinal arachnoiditis is another condition that has not been properly treated. Spinal arachnoiditis is a painful disorder caused by the inflammation of the arachnoid, one of the membranes that surround and protect the nerves of the spinal cord. To date treatments for spinal arachnoiditis are limited.

Thus, there is a need to develop new devices and methods for intervertebral disc treatments or treatments of spinal arachnoiditis that allow accurate and precise implantation of the device at, near, or in the damaged intervertebral disc or in or near the intrathecal space and/or thecal sac resulting in minimal physical and psychological trauma to the patient.

SUMMARY

New devices and methods are provided for intervertebral disc treatments or treatments of spinal arachnoiditis that allow accurate and precise implantation of the device at, near, or in the damaged intervertebral disc or in, at, or near the intrathecal space and/or thecal sac resulting in minimal physical and psychological trauma to the patient.

In some embodiments, the chemonucleolysis agent can be administered in the same cannula or needle without the need to reposition it several times. The chemonucleolysis agent enzymatically degrades the proteoglycans in the nucleus pulposus, which reduces intervertebral disc pressure and, in some embodiments, allows retraction of herniated tissue.

In one embodiment, a device is provided for treating an intervertebral disc in a patient in need of such treatment, the device being biodegradable and implantable within the intervertebral disc, the device comprising a chemonucleolysis agent to enzymatically degrade at least a portion of the intervertebral disc and being configured to immediately release an effective amount of the chemonucleolysis agent within 24 hours and to provide sustained release of the chemonucleolysis agent over a period of up to one year to treat the intervertebral disc.

In a second embodiment, there is a device for treating spinal arachnoiditis in a patient in need of such treatment, the device being implantable in or near an intrathecal space or thecal sac of the patient, the device comprising a chemonucleolysis agent and having an immediate release layer configured to release an effective amount of the chemonucleolysis agent within 24 hours and a sustained release layer contacting the immediate release layer to provide sustained release of the chemonucleolysis agent over a period of up to 3 months to treat the spinal arachnoiditi In another embodiment, a device is provided for treating an intervertebral disc in a patient in need of such treatment, the device being biodegradable and implantable within the intervertebral disc, the device comprising a drug depot comprising a polymer and hyaluronidase to proteolytically degrade at least a portion of a nucleus pulposus of the intervertebral disc, the drug depot having an immediate release layer configured to release an effective amount of the hyaluronidase within 24 hours and a sustained release layer contacting the immediate release layer to provide sustained release of the hyaluronidase over a period of up to 3 months to treat the intervertebral disc.

In yet another embodiment, there is a method for treating an intervertebral disc having a nucleus pulposus and an annulus fibrosis, the method comprising administering an implantable and biodegradable device to the nucleus pulposus, the device comprising a chemonucleolysis agent to proteolytically degrade at least a portion of the intervertebral disc and being configured to immediately release an effective amount of the chemonucleolysis agent within 24 hours and to provide sustained release of the chemonucleolysis agent over a period of up to one year to treat the intervertebral disc.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

Figure 1:
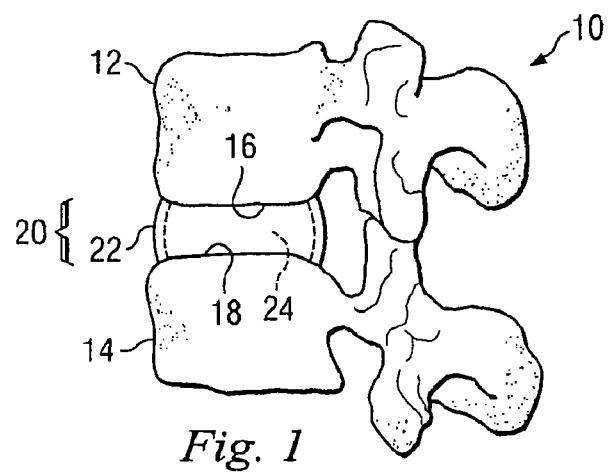
FIG. 1 illustrates a sagittal view of a section of a vertebral column that is damaged and in need of treatment.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

The headings below are not meant to limit the disclosure in any way; embodiments under any one heading may be used in conjunction with embodiments under any other heading.

Definitions

It is noted that, as used in this specification and the appended claims, the singular forms "a," "an," and "the," include plural referents unless expressly and unequivocally limited to one referent. Thus, for example, reference to "a drug depot" includes one, two, three or more drug depots.

An "implantable device" and expressions of like as utilized herein refers to any object implantable through surgical, medical, dental, injection, or other suitable means whose primary function is achieved either through its physical presence or mechanical properties. Implantable devices include one or more drug depots.

A "chemonucleolysis agent", includes, but is not limited to an agent that degrades or causes the dissolution or shrinkage of intervertebral disc or a portion thereof, such as for example, the nucleus pulposus or other tissue in or surrounding the intervertebral disc. In some embodiments, the chemonucleolysis agent will enzymatically degrade or shrink the nucleus pulposus. For example, in some embodiments when the chemonucleolysis agent is an enzyme, it will reduce disc pressure by degrading proteoglycans (PG) so that PGs are not available to hold water. In some embodiments, the chemonucleolysis agent can be a protease or glycanase, which is not proteolytic. In some embodiments, the chemonucleolysis agent, instead of an enzyme, can be an agent that dehydrates the disc, such as for example, a polycationic polymer.

"Analgesic" refers to an agent or compound that can reduce, relieve or eliminate pain. Examples of analgesic agents include but are not limited to acetaminophen, a local anesthetic, such as for example, lidocaine, bupivacaine, ropivacaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, levorphanol, mepiridine, methadone, morphine, nalbuphine, opium, oxycodone, papaveretum, pentazocine, pethidine, phenoperidine, piritramide, dextropropoxyphene, remifentanil, sufentanil, tilidine, tramadol, codeine, dihydrocodeine, meptazinol, dezocine, eptazocine, flupirtine or a combination thereof. Analgesic agents also include those with analgesic and anti-inflammatory properties, such as, for example, amitriptyline, carbamazepine, gabapentin, pregabalin, clonidine, or a combination thereof. The device can include one or more analgesics.

The phrase "anti-inflammatory agent" refers to an agent or compound that has anti-inflammatory effects. The device can include one or more anti-inflammatory agents. These agents may remedy pain by reducing inflammation. Examples of anti-inflammatory agents include, but are not limited to, a statin, sulindac, sulfasalazine, naroxyn, diclofenac, indomethacin, ibuprofen, flurbiprofen, ketoprofen, aclofenac, aloxiprin, aproxen, aspirin, diflunisal, fenoprofen, mefenamic acid, naproxen, phenylbutazone, piroxicam, meloxicam, salicylamide, salicylic acid, desoxysulindac, tenoxicam, ketoralac, clonidine, flufenisal, salsalate, triethanolamine salicylate, aminopyrine, antipyrine, oxyphenbutazone, apazone, cintazone, flufenamic acid, clonixeril, clonixin, meclofenamic acid, flunixin, colchicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, triflumidate, fenamates (mefenamic acid, meclofenamic acid), nabumetone, celecoxib, etodolac, nimesulide, apazone, gold, tepoxalin; dithiocarbamate, or a combination thereof. Anti-inflammatory agents also include other compounds such as steroids, such as for example, fluocinolone, cortisol, cortisone, hydrocortisone, fludrocortisone, prednisone, prednisolone, methylprednisolone, triamcinolone, betamethasone, dexamethasone, beclomethasone, fluticasone interleukin-1 receptor antagonists, thalidomide (a TNF-α release inhibitor), thalidomide analogues (which reduce TNF-α production by macrophages), bone morphogenetic protein (BMP) type 2 or BMP-4 (inhibitors of caspase 8, a TNF-α activator), quinapril (an inhibitor of angiotensin II, which upregulates TNF-α), interferons such as IL-11 (which modulate TNF-a receptor expression), and aurin-tricarboxylic acid (which inhibits TNF-α), guanidinoethyldisulfide, or a combination thereof.

Exemplary anti-inflammatory agents include, for example, naproxen; diclofenac; celecoxib; sulindac; diflunisal; piroxicam; indomethacin; etodolac; meloxicam; ibuprofen; ketoprofen; r-flurbiprofen; mefenamic; nabumetone; tolmetin, and sodium salts of each of the foregoing; ketorolac bromethamine; ketorolac tromethamine; ketorolac acid; choline magnesium trisalicylate; rofecoxib; valdecoxib; lumiracoxib; etoricoxib; aspirin; salicylic acid and its sodium salt; salicylate esters of alpha, beta, gamma-tocopherols and tocotrienols (and all their d, 1, and racemic isomers); methyl, ethyl, propyl, isopropyl, n-butyl, sec-butyl, t-butyl, esters of acetylsalicylic acid; tenoxicam; aceclofenac; nimesulide; nepafenac; amfenac; bromfenac; flufenamate; phenylbutazone, or a combination thereof.

The device can include one or more steroids. Exemplary steroids include, for example, 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, dexamethasone 21-acetate, dexamethasone 21-phosphate di-Na salt, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide or a combination thereof.

The device can include one or more statins. Examples of useful statins for treatment of pain and/or inflammation include, but are not limited to, atorvastatin, simvastatin, pravastatin, cerivastatin, mevastatin (see U.S. Pat. No. 3,883,140, the entire disclosure is herein incorporated by reference), velostatin (also called synvinolin; see U.S. Pat. Nos. 4,448, 784 and 4,450,171 these entire disclosures are herein incorporated by reference), fluvastatin, lovastatin, rosuvastatin and fluindostatin (Sandoz XU-62-320), dalvastain (EP Appin. Publn. No. 738510 A2, the entire disclosure is herein incorporated by reference), eptastatin, pitavastatin, or pharmaceutically acceptable salts thereof or a combination thereof. In various embodiments, the statin may comprise mixtures of (+)R and (−)-S enantiomers of the statin. In various embodiments, the statin may comprise a 1:1 racemic mixture of the statin. Anti-inflammatory agents also include those with anti-inflammatory properties, such as, for example, amitriptyline, carbamazepine, gabapentin, pregabalin, clonidine, or a combination thereof.

In some embodiments, the anti-inflammatory agent can include an "anti-cytokine agent." An anti-cytokine agent includes any molecule, cell, or physical stimulus which decreases, blocks, inhibits, abrogates or interferes with the pro-inflammatory cascade of cytokine proteins leading to an inflammatory response. For example, a suitable "tumor necrosis factor alpha antagonist" or "TNF-alpha" antagonist can bind TNF, and includes anti-TNF antibodies and/or receptor molecules which bind specifically to TNF. A suitable TNF antagonist can also prevent or inhibit TNF synthesis and/or TNF release and includes compounds such as thalidomide, tenidap, or phosphodiesterase inhibitors, such as, but not limited to, pentoxifylline or rolipram.

Anti-cytokine agents include substances that are direct and local-acting modulators of the pro-inflammatory effect of TNF-alpha, such as but not limited to, soluble tumor necrosis factor alpha receptors, any pegylated soluble tumor necrosis factor alpha receptor, monoclonal or polyclonal antibodies or antibody fragments or combinations thereof. Suitable examples include but are not limited to Adalimumab, Infliximab, Etanercept, Pegsunercept (PEG sTNF-R1), sTNF-R1, CDP-870, CDP-571, CNI-1493, RDP58, ISIS 104838, 1, 3-beta-D-glucans, Lenercept, PEG-sTNFRII Fc Mutein, D2E7, Afelimomab, or combinations thereof. They can decrease pain through their actions as inhibitors or agonists of the release of pro-inflammatory molecules. For example, these substances can act by inhibiting or antagonizing expression or binding of cytokines or other molecules that act in the early inflammatory cascade, often resulting in the downstream release of prostaglandins and leukotrienes. These substances can also act, for example, by blocking or antagonizing the binding of excitatory molecules to nociceptive receptors in the nervous system or neuromuscular system, as these receptors often trigger an inflammatory response to inflammation or injury of the nerve or surrounding tissue through a nitric oxide-mediated mechanism. These biological response modifiers include, for example, inhibitors of the action of tumor necrosis factor alpha (TNF-alpha).

In one example of an alternative approach, the anti-cytokine agent is a TNF binding protein. One suitable such anti-cytokine agent is currently referred to as Onercept, Onercept-like agents, and derivatives are all considered acceptable. Still other suitable anti-cytokine agents include dominant-negative TNF variants. A suitable dominant-negative TNF variant includes but is not limited to DN-TNF and including those described by Steed et al. (2003), "Inactivation of TNF signaling by rationally designed dominant-negative TNF variants," Science, 301(5641):1895-1898. Still more embodiments include the use of a recombinant adeno-associated viral (rAAV) vector technology platform to deliver the oligonucleotides encoding inhibitors, enhancers, potentiators, neutralizers, or other modifiers. For example, in one embodiment a rAAV vector technology platform delivers the DNA sequence of a potent inhibitor of tumor necrosis factor (TNF-alpha). One suitable inhibitor is TNFR:Fc. Other anti-cytokine agents interfere with one of the steps in the gene expression and secretion of cytokines, such as transcription, translation, folding, post-translational modification, and intracellular transport. For example, small anti-sense RNA or short interfering RNA (siRNA) can block post-transcriptional processing of cytokine genes. Other anti-cytokine agents include antibodies, including but not limited to naturally occurring or synthetic, double chain, single chained, or fragments thereof. For example, suitable anti-cytokine agents include molecules are based on single chain antibodies called Nanobodies® (Ablynx, Ghent Belgium) which are defined as the smallest functional fragment of a naturally-occurring single domain antibody.

It is understood that TNF is both affected by upstream events which modulate its production and, in turn, affects downstream events. Alternative approaches to treating the disc include using antagonists designed to specifically target TNF as well as molecules upstream, downstream and/or a combination thereof. Such approaches include, but are not limited to modulating TNF directly, modulating kinases, inhibiting cell-signaling, manipulating second messenger systems, modulating kinase activation signals, modulating a cluster designator on an inflammatory cell, modulating other receptors on inflammatory cells, blocking transcription or translation of TNF or other targets in pathway, modulating TNF-alpha post-translational effects, employing gene silencing, or modulating interleukins, for example IL-1, IL-6 and IL-8.

Interleukin-1 is a pro-inflammatory cytokine similar in action to TNF-alpha. For example, certain inhibitors of this protein are similar to those developed to inhibit TNF-alpha. One such example is Kineret® (anakinra) which is a recombinant, non-glycosylated form of the human interleukin-1 receptor antagonist (IL-1Ra). Another suitable anti-cytokine agent is AMG 108, which is a monoclonal antibody that blocks the action of IL-1.

Other suitable anti-cytokine agents include: integrin antagonists, alpha-4 beta-7 integrin antagonists, cell adhesion inhibitors, interferon gamma antagonists, CTLA4-Ig agonists/antagonists (BMS-188667), CD40 ligand antagonists, Humanized anti-IL-6 mAb (MRA, Tocilizumab, Chugai), HMGB-1 mAb (Critical Therapeutics Inc.), anti-IL2R antibody (daclizumab, basilicimab), ABX (anti IL-8 antibody), recombinant human IL-10, and HuMax IL-15 (anti-IL 15 antibody).

Unless otherwise specified or apparent from context, where this specification and the set of claims that follows refer to a drug (e.g., a chemonucleolysis agent, an anti-inflammatory agent, analgesic, or the like) the inventor(s) are also referring to a pharmaceutically acceptable salt of the drug including stereoisomers. Pharmaceutically acceptable salts include those salt-forming acids and bases that do not substantially increase the toxicity of the compound. Some examples of potentially suitable salts include salts of alkali metals such as magnesium, calcium, sodium, potassium and ammonium, salts of mineral acids such as hydrochloric, hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g., p-toluenesulfonic acids, or the like.

"Treating" or treatment of a disease or condition refers to executing a protocol, which may include administering one or more drugs to a patient (human, normal or otherwise, or other mammal), in an effort to alleviate signs or symptoms of the disease. Alleviation can occur prior to signs or symptoms of the disease or condition appearing, as well as after their appearance. Thus, "treating" or "treatment" includes "preventing" or "prevention" of disease or undesirable condition. In addition, "treating" or "treatment" does not require complete alleviation of signs or symptoms, does not require a cure, and specifically includes protocols that have only a marginal effect on the patient. "Reducing pain" includes a decrease in pain and does not require complete alleviation of pain signs or symptoms, and does not require a cure. In various embodiments, reducing pain includes even a marginal decrease in pain. By way of example, the administration of a medical device (e.g., drug depot) containing a chemonucleolysis agent degrades the proteoglycans in the nucleus pulposus, which reduces intervertebral disc pressure and, in some embodiments, allows retraction of herniated tissue, which reduces pain and/or inflammation.

"Localized" delivery includes delivery where one or more devices (e.g., drug depots) containing at least the chemonucleolysis agent is deposited within a tissue, for example, an intervertebral disc, a nucleus pulposus, an annulus fibrosis, or in close proximity (within about 5 cm, or preferably within about 2 cm, for example) thereto. A "targeted delivery system" provides delivery of one or more drugs depots having a quantity of therapeutic agent that can be deposited at or near the target site as needed for treatment of pain, inflammation or other disease or condition.

The term "mammal" refers to organisms from the taxonomy class "mammalian," including but not limited to humans, other primates such as chimpanzees, apes, orangutans and monkeys, rats, mice, cats, dogs, cows, horses, etc. In various embodiments, the mammal is a human patient.

Chemonucleolysis Agent

New compositions and methods for intervertebral disc treatments are provided that allow accurate and precise implantation of a device (e.g., drug depot) comprising a chemonucleolysis agent at, near, or in the damaged intervertebral disc resulting in minimal physical and psychological trauma to the patient.

By the administration of a medical device having the chemonucleolysis agent disposed therein, accurate and precise implantation of the chemonucleolysis agent at, near, or in the damaged intervertebral disc resulting in minimal physical and psychological trauma to the patient can be accomplished. In some embodiments, the chemonucleolysis agent can be administered in the same cannula or needle without the need to reposition it several times. The chemonucleolysis agent degrades the proteoglycans in the nucleus pulposus, which reduces intervertebral disc pressure and pain and/or inflammation and, in some embodiments, allows retraction of herniated tissue.

In one embodiment, a device is provided for treating an intervertebral disc in a patient in need of such treatment, the device being biodegradable and implantable within the intervertebral disc, the device comprising a chemonucleolysis agent to proteolytically degrade at least a portion of the intervertebral disc and being configured to immediately release an effective amount of the chemonucleolysis agent within 24 hours and provide sustained release of the chemonucleolysis agent over a period of up to one year to treat the intervertebral disc.

The device comprises one or more chemonucleolysis agents, which degrade or cause the dissolution or shrinkage of intervertebral disc or a portion thereof, such as for example, the nucleus pulposus or other tissue in or surrounding the intervertebral disc, which reduces intervertebral disc pressure and pain and/or inflammation associated therewith and, in some embodiments, allows retraction of herniated tissue.

Chemonucleolysis agents include, one or more of pancreatic elastase, elastase-2a, elastase-2b, neutrophil elastase, proteinase-3, endogenous vascular elastase, cathepsin G, mast cell chymase, mast cell tryptase, plasmin, thrombin, granzyme B, cathepsin S, cathepsin K, cathepsin L, cathepsin B, cathespin C, cathepsin H, cathespin F, cathepsin G, cathepsin O, cathepsin R, cathepsin V (cathepsin 12), cathepsin W, calpin 1, calpin 2, chondroitinase ABC, chondroitinase AC, hyaluronidase, chymopapain, chymotrypsin, legumain, cathepsin Z (cathepsin X), cathepsin D, cathepsin E, collagenase, matrix metalloproteinases, such as for example, MMP-1 (collagenase-1), MMP-3 (stromelysin-1), MMP-7 (matrilysin), MMP-8 (collagenase-2), MMP-13 (collagenase-3), MMP-18 (collagenase-4), MMP-2 (gelatinase a), MMP-9 (gelatinase b), MMP-3 (stromelysin-1), MMP-10 (stromelysin-2), MMP-11 (stromelysin-3), MMP-7 (matrilysin), MMP-26 (matrilysin), MMP-12 (metalloelastase), MMP-14 (MT1-MMP), MMP-15 (MT2-MMP), MMP-16 (MT3-MMP), MMP-17 (MT4-MMP), MMP-24 (MT5-MMP) transmembrane, MMP-25 (MT6-MMP), gpl anchor, MMP-19, MMP-20 (enamelysin), MMP-x, MMP-23, MMP-27, MMP-28 (epilysin), ADAMTS-1, ADAMTS-2, ADAMTS-3, ADAMTS-4 (aggrecanase-1), ADAMTS-5(aggrecanase-2), ADAMTS-14, papain, subtilisin, subtilisin A, heparanase or a combination thereof.

Chemonucleolysis agents are described in Table 3 of U.S. Ser. No. 12,381,063 filed on Mar. 6, 2009 and published as US 2010/0003237, and U.S. Pat. Nos. 7,572,440, 7,132,098. These entire disclosures are hereby incorporated by reference in the present disclosure. Exemplary chemonucleolysis agents include calpain 1, cathepsin B, cathepsin G, cathepsin L, chondroitinase ABC, chondroitinase AC, chymopapain, chymotrypsin, collagenase, hyaluronidase, MMP-3 (stromelysin-1), MMP-7 (matrilysin), papain, subtilisin, subtilisin A, matrix metalloproteinases or a combination thereof. In some embodiments, the chemonucleolysis agent can be a protease or a glycanase, which is not proteolytic, such as hyaluronidase.

In some embodiments of the methods provided herein, the chemonucleolysis agent is administered in an amount sufficient to maintain a pharmacologically active level of the chemonucleolysis agent locally at the site of implantation in an amount to degrade at least a portion of the intervertebral disc (e.g., nucleus pulposus), which reduces intervertebral disc pressure and, in some embodiments, allows retraction of herniated tissue. This will reduce pain and/or inflammation at the site. For example, the chemonucleolysis agent can be administered in an amount sufficient to maintain a pharmacologically active level of the chemonucleolysis agent at the site of implantation to degrade at least a portion of the nucleus pulposus or be in the plasma in an amount of, for example, at least or about 5 U/mL, 6 U/mL, 7 U/mL, 8 U/mL, 9 U/mL, 10 U/mL, 15 U/mL, 20 U/mL, 30 U/mL, 40 U/mL, 45 U/mL, 50 U/mL or more. In a particular embodiment of the methods, the chemonucleolysis agent is administered in an amount sufficient to maintain a pharmacologically active level of the chemonucleolysis agent at the site of implantation or it can be in the plasma in an amount of at least or about 10 U/mL. In some embodiments, the amount of chemonucleolysis agent released from the device can be measured by measuring it in tissue or body fluid, such as, for example, blood, cerebral spinal fluid, urine, sweat, semen, plasma or a saliva sample taken from the mammal.

In some embodiments of the methods for treating an intervertebral disc in which a chemonucleolysis agent is administered thereto, the chemonucleolysis agent released from the device is 0.02 mg/kg (of the subject), 0.03 mg/kg, 0.04 mg/kg, 0.05 mg/kg, 0.06 mg/kg, 0.07 mg/kg, 0.08 mg/kg, 0.09 mg/kg, 0.1 mg/kg, 0.15 mg/kg, 0.2 mg/kg, 0.25 mg/kg, 0.30 mg/kg, 0.35 mg/kg, 0.40 mg/kg, 0.45 mg/kg, 0.5 mg/kg, 0.55 mg/kg, 0.6 mg/kg, 0.7 mg/kg, 0.8 mg/kg, 0.9 mg/kg, 1.0 mg/kg, 1.1 mg/kg, 1.2 mg/kg, 1.3 mg/kg, 1.4 mg/kg, 1.5 mg/kg or more. In one example, the amount of chemonucleolysis agent administered is 0.05 mg/kg-0.8 mg/kg.

In some embodiments of the methods provided herein, the chemonucleolysis agent is hyaluronidase. Hyaluronidase is available from various manufactures and is described in U.S. Pat. Nos. 7,767,429; 7,169,405; 7,132,098; 7,572,440; 6,958,149; and U.S. Publication Nos. US20040268425; US20100003238; US20090214505; US20100003237; and WO/2009/111066. The entire disclosures of these patents and publications are herein incorporated by reference in their entirety into the present disclosure. One form of hyaluronidase suitable for use in the device is available from Halozyme Therapeutics, Inc. (IL USA), which is a recombinant human hyaluronidase glycoprotein enzyme platform (rHuPH20). The hyaluronidase can be pegylated or a pegylated variant and incorporated into the device (e.g., drug depot).

In some embodiments of the methods provided herein, the hyaluronidase is administered in an amount sufficient to maintain a pharmacologically active level of the hyaluronidase locally at the site of implantation in an amount to degrade at least a portion of the intervertebral disc (e.g., nucleus pulposus), which reduces intervertebral disc pressure and, in some embodiments, allows retraction of herniated tissue. This will reduce pain and/or inflammation at the site. For example, the hyaluronidase can be administered in an amount sufficient to maintain a pharmacologically active level of the hyaluronidase at the site of implantation to degrade at least a portion of the nucleus pulposus or it can be in the plasma in an amount of, for example, at least or about 5 U/mL, 6 U/mL, 7 U/mL, 8 U/mL, 9 U/mL, 10 U/mL, 15 U/mL, 20 U/mL, 30 U/mL, 40 U/mL, 45 U/mL, 50 U/mL or more. In a particular embodiment of the methods, the hyaluronidase is administered in an amount sufficient to maintain a pharmacologically active level of the hyaluronidase at the site of implantation or it can be in the plasma in an amount of at least or about 10 U/mL.

In some embodiments of the methods for treating an intervertebral disc in which a hyaluronidase is administered thereto, the hyaluronidase released from the device is 0.02 mg/kg (of the subject), 0.03 mg/kg, 0.04 mg/kg, 0.05 mg/kg, 0.06 mg/kg, 0.07 mg/kg, 0.08 mg/kg, 0.09 mg/kg, 0.1 mg/kg, 0.15 mg/kg, 0.2 mg/kg, 0.25 mg/kg, 0.30 mg/kg, 0.35 mg/kg, 0.40 mg/kg, 0.45 mg/kg, 0.5 mg/kg, 0.55 mg/kg, 0.6 mg/kg, 0.7 mg/kg, 0.8 mg/kg, 0.9 mg/kg, 1.0 mg/kg, 1.1 mg/kg, 1.2 mg/kg, 1.3 mg/kg, 1.4 mg/kg, 1.5 mg/kg or more. In one example, the amount of hyaluronidase administered is 0.05 mg/kg-0.8 mg/kg.

In some embodiments, the device (e.g., drug depot) may comprise hyaluronic acid, hyaluronan, or hyaluronic acid polymers having a MW of 100,000 to 10,000,000.

In some embodiments, the chemonucleolysis agent, instead of an enzyme, can be an agent that dehydrates the disc, such as for example, a polycationic polymer. Polycationic polymers have a positive charge that interacts with the negatively charged proteoglycans (PGs) in the nucleus pulposus, which results in the water being displaced through a combination of electrostatic and osmotic mechanisms. With a polycationic polymer, the PGs are not degraded, but the water is prevented from associating with the PGs. In both cases, the nucleus pulposus shrinks.

In some embodiments, the size of the nucleus pulposus herniation is reduced by about 15-20%, 20-25%, 25-30%, 30-35%, 35-40%, 45-50%, 55-60%, 65-70%, 75-80%, 85-90%, or 95-100% or the herniated intervertebral disc completely resolves.

Some polycationic polmers include, but are not limited to, a polymer of an amino acid, such as D-lysine, L-lysine, D-arginine, L-arginine, D-histidine, or L-histidine or a combination thereof. In some embodiments, the cationic polymer comprises dextran, an arabinogalactan, a pullulan, a cellulose, an inulin, a chitosan, an ornithine polymer, a spermine polymer, a spermidine polymer, or polyethylenimine or a combination thereof. Some cationic polymers are described in US 2007/0258941 (U.S. Ser. No. 11/799,393 filed May 1, 2007). The entire disclosure is herein incorporated by reference into the present disclosure.

In certain embodiments, the cationic polymer is at least about 2 kDa in average size. For example, the polymer is at least about 300 kDa in size. An exemplary polymer is a polylysine, comprising, for example, at least one of D-lysine and L-lysine monomers. Thus the polymer for example the polylysine, is about 100 kDa to about 300 kDa in size.

For administration of the cationic compound, the dosage ranges from about 0.0001 to 100 mg/kg, and more usually 0.01 to 5 mg/kg, of the subject body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regimen entails a single administration or administration once per week, once every two weeks, once every three weeks, once every four weeks, once a month, once every 3 months or once every three months to 6 months. Dosage regimens for a cationic compound of the invention include about 1 mg/kg body weight or about 3 mg/kg body weight by intervertebral or intrathecal administration.

In some embodiments, the chemonucleolysis agent and optionally one or more additional therapeutic agents (e.g., growth factor, analgesic, anti-inflammatory agent, etc.) are included in a device that is a drug depot. A "drug depot" comprises the composition in which at least one therapeutic agent or active pharmaceutical ingredient or drug is administered to the body. Thus, a drug depot may comprise a physical structure to facilitate implantation and retention in a desired site (e.g., a disc space, a spinal canal, a tissue of the patient, or site of pain and/or inflammation, etc.). The drug depot also comprises the drug itself. The term "drug" as used herein is generally meant to refer to any substance that alters the physiology of a patient. The term "drug" may be used interchangeably herein with the terms "therapeutic agent," "therapeutically effective amount," and "active pharmaceutical ingredient" or "API." It will be understood that unless otherwise specified a "drug" formulation may include more than one therapeutic agent, wherein exemplary combinations of therapeutic agents include a combination of two or more drugs. The drug provides a concentration gradient of the therapeutic agent (e.g., chemonucleolysis agent) for delivery to the site. In various embodiments, the drug depot provides an optimal drug concentration gradient of the therapeutic agent at a distance of up to about 0.1 cm to about 5 cm from the implant site, and comprises at least one therapeutic agent or its pharmaceutically acceptable salt.

The term "therapeutic agent" includes any molecule, protein, growth factor, etc. which would be contemplated for administration in, at or near the intervertebral disc of a mammal. Such examples would include, but are not limited to one or more chemonucleolysis agents, growth factors, anti-inflammatory agents (e.g., NSAIDS), antibiotics, analgesics, muscle relaxants, or the like, as well as any molecule or cell, which decreases, blocks, inhibits, abrogates or interferes with the pro-inflammatory cascade of proteins leading to an inflammatory response. For example, a suitable TNF-α antagonist can bind TNF-α, and includes anti-TNF-α antibodies and/or receptor molecules which bind specifically to TNF-α, as well as small molecules which antagonize TNF-α activity. A suitable TNF-α antagonist can also prevent or inhibit TNF-α synthesis and/or TNF-α release. Another example may also provide for any cytokine or biologically active fragment thereof which possesses the ability to decrease, block, inhibit, abrogate or interfere with the pro-inflammatory response promoted by other cytokine proteins (e.g., IL-10, IL-4, IL-13 and TGF-β) as well as any molecule, cell, which positively modulates the anti-inflammatory effect of such an anti-inflammatory cytokine so as to impart an increase in the ability to reduce patient inflammation and/or pain.

The therapeutic agent may comprise growth factors that modulate the growth or differentiation of other cells, particularly connective tissue progenitor cells. The therapeutic agent may include, but is not limited to, members of the fibroblast growth factor family, including acidic and basic fibroblast growth factor (FGF-1 and FGF-2) and FGF-4, members of the platelet-derived growth factor (PDGF) family, including PDGF-AB, PDGF-BB and PDGF-AA; EGFs; the TGF-β superfamily, including TGF-β1, 2 or 3; osteoid-inducing factor (OIF); angiogenin(s); endothelins; hepatocyte growth factor or keratinocyte growth factor; members of the bone morphogenetic proteins (BMP's) BMP-1, BMP-3, BMP-2; OP-1, BMP-2A, BMP-2B, or BMP-7; HBGF-1 or HBGF-2; growth differentiation factors (GDF's); members of the hedgehog family of proteins, including indian, sonic and desert hedgehog; ADMP-1; other members of the interleukin (IL) family; or members of the colony-stimulating factor (CSF) family, including CSF-1, G-CSF, and GM-CSF, or isoforms thereof; or VEGF, NELL-1 (neural epidermal growth factor-like 1), CD-RAP (cartilage-derived retinoic acid-sensitive protein) or combinations thereof.

In some embodiments, the device comprises a chemonucleolysis agent and growth factors (e.g., osteogenic protein). Exemplary osteogenic proteins include, but are not limited to, OP-1, OP-2, OP-3, BMP-2, BMP-3, BMP-3b, BMP-4, BMP-5, BMP-6, BMP-9, BMP-10, BMP-11, BMP-12, BMP-13, BMP-14, BMP-15, GDF-1, GDF-2, GDF-3, GDF-5, GDF-6, GDF-7, GDF-8, GDF-9, GDF-10, GDF-11, GDF-12, CDMP-1, CDMP-2, CDMP-3, DPP, Vg-1, Vgr-1, 60A protein, NODAL, UNIVIN, SCREW, ADMP, NEURAL, and TGF-beta. As used herein, the terms "morphogen, " "bone morphogen, " "BMP, " "osteogenic protein" and "osteogenic factor" embrace the class of proteins typified by human osteogenic protein 1 (hOP-1) and are described in U.S. Pat. No. 7,572,440. The entire disclosure is hereby incorporated by reference in the present disclosure.

Exemplary growth factors include, but are not limited to, members of the transforming growth factor beta family, including bone morphogenetic protein 2 (BMP-2); bone morphogenetic protein 4 (BMP-4); and transforming growth factors beta-1, beta-2, and beta-3 (potent keratinocyte growth factors). Other useful members of the transforming growth factor beta family include BMP-3, BMP-5, BMP-6, BMP-9, DPP, Vg1, Vgr, 60A protein, GDF-1, GDF-3, GDF-5, GDF-6, GDF-7, CDMP-1, CDMP-2, CDMP-3, BMP-10, BMP-11, BMP-13, BMP-15, Univin, Nodal, Screw, ADMP, Neural, and amino acid sequence variants thereof. Other growth factors include epidermal growth factor (EGF), which induces proliferation of both mesodermal and ectodermal cells, particularly keratinocytes and fibroblasts; platelet-derived growth factor (PDGF), which exerts proliferative effects on mesenchymal cells; fibroblast growth factor (FGF), both acidic and basic; and insulin-like growth factor 1 (IGF-1) or 2 (IGF-2), which mediate the response to growth hormone, particularly in bone growth. Further growth factors include osteogenic proteins. A particularly preferred osteogenic protein is OP-1, also known as bone morphogenetic protein 7 (BMP-7). OP-1 is a member of the transforming growth factor beta gene superfamily. It is a 139 amino acid residue long homodimer of MW 36,000. OP-1 induces new bone formation in vivo and promotes the repair of diaphyseal segmental bone defects and is described in U.S. Pat. No. 7,132,098. The entire disclosure is hereby incorporated by reference in the present disclosure.

In some embodiments, the therapeutic agent can comprise cells. Suitable cells include, without limitation, mesenchymal stem cells, periosteal cells, pluripotent stem cells, embryonic stem cells, osteoprogentior cells, osteoblasts, osteoclasts, bone marrow-derived cell lines, or any combination thereof. Other therapeutic agents include, for example, DNA, RNA, and their derivatives; vehicles for gene therapy, agents for inducing cell differentiation or de-differentiation or the like.

The therapeutic agent may also comprise nutrients such as chondroitin sulfate and/or glucosamine. The therapeutic agent can also include a lubricant including, but not limited to, lubricin, polyethylene glycol, or any combinations thereof.

In one embodiment, the therapeutic agent in the depot includes a chemonucleolysis agent, an anti-inflammatory, an anti-apoptotic, a proliferative agent, a fibrosis initiating agent, a differentiating agent, a gene therapy agent, a lubricating agent, a nutrient, an anti-innervating agent, a hygroscopic agent, or a combination thereof.

A depot contains one or more therapeutic agent(s), as discussed above. A "depot" includes but is not limited to capsules, coatings, matrices, wafers, sheets, strips, ribbons, pills, pellets, microspheres, or other pharmaceutical delivery system or a combination thereof. Suitable materials for the depot are ideally pharmaceutically acceptable biodegradable and/or any bioabsorbable materials that are preferably FDA approved or GRAS materials. These materials can be polymeric or non-polymeric, as well as synthetic or naturally occurring, or a combination thereof. Typically, the depot will be a solid or semi-solid formulation comprising a biocompatible material that can be biodegradable. The term "solid" is intended to mean a rigid material, while "semi-solid" is intended to mean a material that has some degree of flexibility, thereby allowing the depot to bend and conform to the surrounding tissue requirements.

Suitable drug depots useful in the present application are described in U.S. Ser. No. 12,105,474 filed Apr. 18, 2008 and published as U.S. Publication No. 20090263489, and U.S. Ser. No. 12/396,122, filed Mar. 2, 2009 and published as US20090263459. The entire disclosure of these applications is incorporated by reference herein in their entirety.

The drug depot may be microspheres or contain microspheres. Microspheres include generally spherical particles about 10 microns to about 2000 microns, or 10 microns to 1000 microns, or 50 microns to 250 microns and at least a population of microspheres in a diameter permitting parenteral administration. The process used to make the microspheres can be controlled to achieve a particular desired size range of microspheres. Other methods, such as sieving, can be used to more tightly control the size range of the microspheres.

In some embodiments, the drug depot comprises microspheres of a size range of from about 100 to 400 microns, which is well suited for delivery to the target tissue sites.

Microspheres comprise a hollow space encapsulated by lipids, polymers, or at least one surfactant, or any combination thereof, wherein the hollow space comprises a therapeutic agent (e.g., chemonucleolysis agent). In different embodiments, microspheres may include microbubbles or liposomes.

In some embodiments, the microspheres contain the therapeutic agent (e.g., chemonucleolysis agent) and can comprise a polymer, without limitation, poly(alpha-hydroxy acid), polyhydroxybutyric acid, polycaprolactone, poly(propylene fumarate), PEG, polyorthoester, polyanhydride, polyvinyl alcohol and ethylenevinyl acetate, or the like or combinations or copolymers thereof. In some embodiments, the microsphere can be derived from a poly(alpha-hydroxy acid), in particular, from a poly(lactide) ("PLA") or a copolymer of D,L-lactide and glycolide or glycolic acid, such as a poly(D, L-lactide-co-glycolide) ("PLG" or "PLGA"), or a copolymer of D,L-lactide and caprolactone. The microspheres may be derived from any of various polymeric starting materials which have a variety of molecular weights and, in the case of the copolymers such as PLG, a variety of lactide:glycolide ratios, the selection of which will be largely a matter of choice, depending in part on the desired dose of the active ingredient(s).

In some embodiments, the microspheres containing the chemonucleolysis agent are loaded into the formulation and are disposed uniformly throughout it or in a particular region (e.g., center or borders) and delivered in, at, or near the intervertebral disc. The microspheres will degrade and release the therapeutic agent at, near or in the intervertebral disc (e.g., nucleus pulposus, annulus fibrosis) and the microspheres will begin releasing the therapeutic agent immediately and/or in a sustained release fashion to the desired tissue location.

The drug depot comprises a therapeutically effective amount of the therapeutic agent. A "therapeutically effective amount" or "effective amount" is such that when administered, the drug results in alteration of the biological activity, such as, for example, inhibition of inflammation, reduction or alleviation of pain, improvement in the condition through muscle relaxation, degradation of a portion of the nucleus pulposus, etc. The dosage administered to a patient can unless otherwise specified or apparent from context be as single or multiple doses depending upon a variety of factors, including the drug's administered pharmacokinetic properties, the route of administration, patient conditions and characteristics (sex, age, body weight, health, size, etc.), extent of symptoms, concurrent treatments, frequency of treatment and the effect desired. In one embodiment, the therapeutic agent can be in the depot and used in an amount typically ranging between about 0.1 to 5000 mcg/kg of body weight or about 1 to 1000 mcg/kg of body weight or about 10 to 500 mcg/kg of body weight or about 50 to 250 mcg/kg of body weight.

In some embodiments the formulation of the drug depot is designed for immediate release. In other embodiments the formulation is designed for sustained release. In other embodiments, the formulation comprises one or more immediate release surfaces or layers and one or more sustain release surfaces or layers in one depot.

The phrases "sustained release" or "sustain release" (also referred to as extended release or controlled release) are used herein to refer to one or more therapeutic agent(s) that is introduced into the body of a human or other mammal and continuously or continually releases a stream of one or more therapeutic agents (e.g., chemonucleolysis agents) over a predetermined time period and at a therapeutic level sufficient to achieve a desired therapeutic effect throughout the predetermined time period. Reference to a continuous or continual release stream is intended to encompass release that occurs as the result of biodegradation in vivo of the drug depot, or a matrix or component thereof, or as the result of metabolic transformation or dissolution of the therapeutic agent(s) or conjugates of therapeutic agent(s). As persons of ordinary skill are aware, sustained release formulations may, by way of example, be created as films, slabs, pellets, microparticles, microspheres, microcapsules, spheroids, shaped derivatives or pastes. Further, the formulations may be used in conjunction with any implantable, or insertable system that a person of ordinary skill would appreciate as useful in connection with embodiments herein including but not limited to parenteral formulations, microspheres, microcapsules, pastes, implantable rods, pellets, plates or fibers, etc. The chemonucleolysis agent can be in the device as a sustained release formulation, where one or more regions or layers of the device release the chemonucleolysis agent into the intervertebral disc to degrade the nucleus pulposus over an extended period of time (e.g., 3 months to 1 year).

The immediate release therapeutic agent can be released first. The phrase "immediate release" is used herein to refer to one or more therapeutic agent(s) that is introduced into the body and that is allowed to dissolve in or become absorbed at the location to which it is administered, with no intention of delaying or prolonging the dissolution or absorption of the drug. Immediate release refers to the release of drug within a short time period following administration, e.g., generally within a few seconds or minutes to about 1, 2, 3, 4, 5, 6, 7, 8, 9, 10, 11, 12 hours or within 24 hours after implantation. The chemonucleolysis agent can be in the device as an immediate release formulation, where one or more regions or layers of the device release the chemonucleolysis agent into the intervertebral disc to degrade the nucleus pulposus. The immediate release region or layer of the device can be in liquid solutions, suspensions, or emulsions forms or semi-solid or solid forms having a suitable excipient for immediate release. Suitable excipients are, for example, water, saline, dextrose, glycerol, ethanol, pH buffering agents, metal ion salts, or other such buffers. The formulation also may contain other minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate, cyclodextrins or a combination thereof.

For example, an immediate release formulation of a chemonucleolysis agent that can be incorporated into a drug depot can be hyaluronidase formulated with one or more of EDTA, NaCl, $CaCl_2$, histidine, lactose, albumin, Pluronic® F68, TWEEN® and/or other detergent or other similar agents. For example, compositions provided herein can contain one or more pH buffers (such as, for example, histidine, phosphate, or other buffers), or acidic buffer (such as acetate, citrate, pyruvate, Gly-HCl, succinate, lactate, maleate or other buffers), tonicity modifier (such as, for example, an amino acid, polyalcohol, NaCl, trehalose, other salts and/or sugars), stabilizer, chelating agent, such as ethylenediaminetetraacetic acid, ethylenediaminetetraacetate or calcium EDTA, oxygen scavenger, such as methionine, ascorbic acid/ascorbate, citric acid/citrate, or albumin, and/or a preservative, such as preservative containing an aromatic ring (e.g. phenol or cresol). In some embodiments, the depot does not contain any preservatives and, therefore, is preservative free.

Exemplary stabilizers that are useful for the depot containing the chemonucleolysis agent include, for example, polysorbates or proteins such as human serum albumin. Exemplary concentrations of serum albumin that are useful in the compositions herein include 0.1 mg/mL, 0.2 mg/mL, 0.3 mg/mL, 0.4 mg/mL, 0.5 mg/mL, 0.6 mg/mL, 0.7 mg/mL, 0.8 mg/mL, 0.9 mg/mL or 1 mg/mL, but can be more or less. Polysorbates also can be present in the depot at, for example, concentrations of or about 0.001%, 0.002%, 0.003%, 0.004%, 0.005%, 0.006%, 00.007%, 0.008%, 0.009%, 0.01%, 0.02%, 0.03%, 0.04%, 0.05%, 0.06%, 0.07%, 0.08%, 0.09% or 0.1%. A metal chelating agent, such as calcium EDTA (CaEDTA), also can be present, such as for example, at concentrations of between approximately 0.02 mM to 20 mM, such as 0.02 mM, 0.04 mM, 0.06 mM, 0.08 mM, 0.1 mM, 0.2 mM, 0.3 mM, 0.4 mM, 0.5 mM, 0.6 mM, 0.7 mM, 0.8 mM, 0.9 mM, 1 mM, 5 mM, 10 mM, 15 mM, 20 mM or more. The pH and the osmolarity of the depot can be adjusted to optimize the conditions for the desired activity and stability of the overall composition. In some embodiments, the compositions provided herein have an osmolarity of at or about 100 mOsm/kg, 120 mOsm/kg, 140 mOsm/kg, 160 mOsm/kg, 180 mOsm/kg, 200 mOsm/kg, 220 mOsm/kg, 240 mOsm/kg, 260 mOsm/kg, 280 mOsm/kg, 300 mOsm/kg, 320 mOsm/kg, 340 mOsm/kg, 360 mOsm/kg, 380 mOsm/kg, 400 mOsm/kg, 420 mOsm/kg, 440 mOsm/kg, 460 mOsm/kg, 500 or more mOsm/kg, and a pH of at or about 6, 6.2, 6.4, 6.6, 6.8, 7, 7.2, 7.4, 7.6, 7.8 or 8.

Generally NaCl can be provided in formulations herein, for example, in an amount that is or is about 100 mM-150 mM or more. For example, an exemplary formulation can contain at or about 10 mM histidine and/or at or about 130 mM NaCl. Other formulations can contain in addition or alternatively lactose, for example, at or about 13 mg/ml. Additionally, an anti-bacterial or anti-fungal agent, including, but not limited to thiomersal, can be present in the formulation. Formulations can further contain Albumin, Pluronic ® F68, TWEEN ® and/or other detergent. The formulations are provided at a pH that is or is about 6.0, 6.1., 6.2, 6.3, 6.4, 6.5, 6.6, 6.7, 6.8, 6.9, 7.0, 7.1, 7.2, 7.3 or 7.4, generally that is or is about pH 6.5. In some embodiments, the drug depot containing the chemonucleolysis agent is designed for local administration into the intervertebral disc.

The depot can be designed to provide the desired release rate profile for immediate release and/or sustained release of the therapeutic agent (e.g., chemonucleolysis agent, analgesic, anti-inflammatory agent, growth factor, etc.). The phrase "release rate profile" refers to the percentage of active ingredient that is released over fixed units of time, e.g., mcg/hr, mcg/day, mg/hr, mg/day, 10% per day for ten days, and the like. As persons of ordinary skill know, a release rate profile may be but need not be linear. By way of a non-limiting example, the drug depot may be a pellet that releases at least one chemonucleolysis agent, analgesic, anti-inflammatory agent, growth factor, and/or analgesic agent in a bolus dose and at least one chemonucleolysis agent, analgesic, anti-inflammatory agent, and/or growth factor over an extended period of time (e.g., 3 days to 3 months).

The depot can be biodegradable. The term "biodegradable" includes that all or parts of the drug depot will degrade over time by the action of enzymes, by hydrolytic action and/or by other similar mechanisms in the human body. In various embodiments, "biodegradable" includes that the depot can break down or degrade within the body to non-toxic components after or while a therapeutic agent has been or is being released. By "bioerodible" it is meant that the depot will erode or degrade over time due, at least in part, to contact with substances found in the surrounding tissue, fluids or by cellular action. By "bioabsorbable" it is meant that the depot will be broken down and absorbed within the human body, for example, by a cell or tissue. "Biocompatible" means that the depot will not cause substantial tissue irritation or necrosis at the target tissue site.

The depot may comprise non-biodegradable material. Examples of non-biodegradable polymers include, but are not limited to, various cellulose derivatives (carboxymethyl cellulose, cellulose acetate, cellulose acetate propionate, ethyl cellulose, hydroxypropyl methyl cellulose, hydroxyalkyl methyl celluloses, and alkyl celluloses), silicon and silicon-based polymers (such as polydimethylsiloxane), polyethylene-co-(vinyl acetate), poloxamer, polyvinylpyrrolidone, poloxamine, polypropylene, polyamide, polyacetal, polyester, poly ethylene-chlorotrifluoroethylene, polytetrafluoroethylene (PTFE or "Teflon™"), styrene butadiene rubber, polyethylene, polypropylene, polyphenylene oxide-polystyrene, poly-α-chloro-p-xylene, polymethylpentene, polysulfone, non-degradable ethylene-vinyl acetate (e.g., ethylene vinyl acetate disks and poly(ethylene-co-vinyl acetate)), and other related biostable polymers.

Non-resorbable polymers can also include, but are not limited to, delrin, polyurethane, copolymers of silicone and polyurethane, polyolefins (such as polyisobutylene and polyisoprene), acrylamides (such as polyacrylic acid and poly (acrylonitrile-acrylic acid)), neoprene, nitrile, acrylates (such as polyacrylates, poly(2-hydroxy ethyl methacrylate), methyl methacrylate, 2-hydroxyethyl methacrylate, and copolymers of acrylates with N-vinyl pyrrolidone), N-vinyl lactams, polyacrylonitrile, glucomannan gel, vulcanized rubber and combinations thereof. Examples of polyurethanes include thermoplastic polyurethanes, aliphatic polyurethanes, segmented polyurethanes, hydrophilic polyurethanes, polyether-urethane, polycarbonate-urethane and silicone polyether-urethane. Other suitable non-resorbable material include, but are not limited to, lightly or highly cross-linked biocompatible homopolymers and copolymers of hydrophilic monomers such as 2-hydroxyalkyl acrylates and methacrylates, N-vinyl monomers, and ethylenically unsaturated acids and bases; polycyanoacrylate, polyethylene oxide-polypropylene glycol block copolymers, polygalacturonic acid, polyvinyl pyrrolidone, polyvinyl acetate, polyalkylene glycols, polyethylene oxide, collagen, sulfonated polymers, vinyl ether monomers or polymers, alginate, polyvinyl amines, polyvinyl pyridine, and polyvinyl imidazole. Depending on the amount of crosslinking within the bioresorbable polymers, the degradation time of the polymer can be reduced, thus making the polymer, for the purpose of this application, appear to be non-resorbable over the time frame of the use of the material for this invention.

The drug depot can provide the appropriate pain management medication. The phrase "pain management medication" includes one or more therapeutic agents that are administered to prevent, alleviate or remove pain entirely. These include anti-inflammatory agents, analgesics, anesthetics, narcotics, and so forth, or combinations thereof.

In various embodiments, the depot can be designed to cause an initial burst dose of one or more therapeutic agents within the first 24 hours after implantation. "Initial burst" or "burst effect" or "bolus dose" or "pulse dose" refer to the release of therapeutic agent from the depot during the first 24 hours after the depot comes in contact with an aqueous fluid (e.g., cerebral spinal fluid, nucleus pulposus, etc.). The burst effect may be an immediate release. The "burst effect" is believed to be due to the increased release of therapeutic agent from the depot. The initial burst effect or bolus dose may be determined beforehand by formulating the depot by calculating the quotient obtained by dividing (i) the effective amount by weight of therapeutic agent to be released from the depot or region in a predetermined initial period of time after implantation of the depot, by (ii) the total amount of therapeutic agent that is to be delivered from an implanted composition. It is understood that the initial burst may vary depending on the shape and surface area of the implant.

The burst effect with respect to the region of the depot or individual depot, in various embodiments, can be designed so that a larger initial dose may be released over a short period of time to achieve the desired effect. For example, if a drug depot is designed to release 15 mg of chemonucleolysis agent per 48 hours, then the initial burst dose or bolus dose region or depot will be designed to release a percentage of the dose within the first 24 hours (e.g., 10 mg of chemonucleolysis agent or 66% of the 48 hour dose within 24 hours). Thus, the burst effect of the drug depot or region of the drug depot releases more therapeutic agent than the sustained release region or depot.

A region or depot that utilizes a burst effect or bolus dose will release more therapeutic agent (e.g., chemonucleolysis agent, analgesic, anti-inflammatory, and/or growth factor)

than the sustained release region or depot. For example, particularly with painful conditions such as discogenic back pain, or the like, the initial burst effect of the drug depot or region of the drug depot will be advantageous as it will provide more immediate pain and/or inflammation relief as a bolus dose of drug will be released at or near the target tissue site and provide the desired reducing, or alleviation of signs or symptoms of pain and/or inflammation. For example, the drug depot or region of the drug depot may release 51%, 52%, 53%, 54%, 55%, % 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% of the daily dose within the first one to twelve hours to reduce, prevent or treat pain and/or inflammation.

In some embodiments, the drug depot may have an initial burst effect to release the drug shortly after it is implanted. Various factors can be adjusted to achieve the initial burst of therapeutic agent release. First, the initial burst can be controlled by factors related to the property of the depot, such as the water immiscibility of the solvent, polymer/solvent ratio, and the property of the polymer. The extent of water immiscibility of the solvent used in the depot affects that rate aqueous body fluid can penetrate the depot to release the therapeutic agent. Generally, higher water solubility leads to a higher initial burst while water immiscibility leads to a lower initial burst or slower release (sustained release) of the therapeutic agent.

Suitable solvents that can be used to control initial burst release or sustained release include, but are not limited to, methyl benzoate, ethyl benzoate, n-propyl benzoate, isopropyl benzoate, butyl benzoate, isobutyl benzoate, sec-butyl benzoate, tert-butyl benzoate, isoamyl benzoate, benzyl benzoate, water, alcohol, low molecular weight PEG (less than 1,000 MW), triacetin, diacetin, tributyrin, triethyl citrate, tributyl citrate, acetyl triethyl citrate, acetyl tributyl citrate, triethylglycerides, triethyl phosphate, diethyl phthalate, diethyl tartrate, mineral oil, polybutene, silicone fluid, glycerin, ethylene glycol, octanol, ethyl lactate, propylene glycol, propylene carbonate, ethylene carbonate, butyrolactone, ethylene oxide, propylene oxide, N-methyl-2-pyrrolidone, 2-pyrrolidone, glycerol formal, methyl acetate, ethyl acetate, methyl ethyl ketone, dimethylformamide, glycofurol, dimethyl sulfoxide, tetrahydrofuran, caprolactam, decylmethyl-sulfoxide, oleic acid, 1-dodecylazacyclo-heptan-2-one, or mixtures thereof. The solvent can be mixed, in various embodiments, with the therapeutic agent and/or polymers to obtain the desired release profile.

The depot may have pore forming agents, which include biocompatible materials that when contacted with body fluids dissolve, disperse or degrade to create pores or channels in the polymer matrix. Typically, organic and non-organic materials that are water soluble such as sugars (e.g., sucrose, dextrose), water soluble salts (e.g., sodium chloride, sodium phosphate, potassium chloride, and sodium carbonate), water soluble solvents such as N-methyl-2-pyrrolidone and polyethylene glycol and water soluble polymers (e.g., carboxymethylcellulose, hydroxypropyl-cellulose, and the like) can conveniently be used as pore formers. Such materials may be present in amounts varying from about 0.1% to about 100% of the weight of the polymer, but will typically be less than 50% and more typically less than 10-20% of the weight of polymer.

Further, varying the molecular weight of the polymer in the depot, or adjusting the molecular weight distribution of the polymer material in the depot vehicle can affect the initial burst and the release rate of therapeutic agent from the depot. Generally, a higher molecular weight polymer renders a lower initial burst and slower release rate of the therapeutic agent. The polymers may have different end groups such as acid and ester end groups. As persons of ordinary skill in the art are aware, implantable elastomeric depot compositions having a blend of polymers with different end groups are used the resulting formulation will have a lower burst index and a regulated duration of delivery. For example, one may use polymers with acid (e.g., carboxylic acid) and ester end groups (e.g., methyl of ethyl ester end groups).

Additionally, by varying the comonomer ratio of the various monomers that form a polymer (e.g., the L/G (lactic acid/glycolic acid) or G/CL (glycolic acid/polycaprolactone) ratio for a given polymer) there will be a resulting depot composition having a regulated burst index and duration of delivery. For example, a depot composition having a polymer with a L/G ratio of 50:50 may have a short duration of delivery ranging from about two days to about one month; a depot composition having a polymer with a L/G ratio of 65:35 may have a duration of delivery of about two months; a depot composition having a polymer with a L/G ratio of 75:25 or L/CL ratio of 75:25 may have a duration of delivery of about three months to about four months; a depot composition having a polymer ratio with a L/G ratio of 85:15 may have a duration of delivery of about five months; a depot composition having a polymer with a L/CL ratio of 25:75 or PLA may have a duration of delivery greater than or equal to six months; a depot composition having a terpolymer of CL/G/L with G greater than 50% and L greater than 10% may have a duration of delivery of about one month and a depot composition having a terpolymer of CL/G/L with G less than 50% and L less than 10% may have a duration months up to six months. In general, increasing the G content relative to the CL content shortens the duration of delivery whereas increasing the CL content relative to the G content lengthens the duration of delivery. Thus, among other things, depot compositions having a blend of polymers having different molecular weights, end groups and comonomer ratios can be used to create a depot formulation having a lower burst index and a regulated duration of delivery.

Factors such as the particle size, the disintegration of the particulates, the morphology of the particulates (e.g., whether pores are present in the particulates before implanting or can be formed easily by body fluid attack), coatings, complex formation by the therapeutic agent and the strength of complex bond, can be manipulated to achieve the desired low initial burst and release rate.

The drug depot may comprise at least one analgesic agent or its pharmaceutically acceptable salt. Examples of analgesic agents include but are not limited to acetaminophen, a local anesthetic, such as for example, lidocaine, bupivacaine, ropivacaine, opioid analgesics such as amitriptyline, carbamazepine, gabapentin, pregabalin, clonidine, opioid analgesics or a combination thereof. Opioid analgesics include, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacyl-morphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tilidine, tramadol or a combination thereof. Analgesic agents also include those with analgesic and anti-inflammatory properties, such as, for example, amitriptyline, carbamazepine, gabapentin, pregabalin, clonidine, or a combination thereof.

In some embodiments, the drug depot contains anti-inflammatory agents and/or analgesic comprising flurbiprofen, indoprofen, naproxol, pentazocine, proxazole, tramadol, verilopam, volazocine, xylazine, zucapsaicin, phenyhydantoin, phenobarbital, primidone, ethosuximide, methsuximide, phensuximide, trimethadione, diazepam, benzodiazepines, phenacemide, pheneturide, acetazolamide, sulthiame, bromide, nalorphine, naloxone, naltrexone, salycilates, phenylbutazone, indomethacin, phenacetin, dextropropoxyphene, levomethadyl, pethidine, remifentanil, flupirtine or a combination thereof.

In some embodiments, the anti-inflammatory and/or analgesic agents include, but are not limited to, salicylates, diflunisal, indomethacin, ibuprofen, naproxen, tolmetin, ketorolac, diclofenac, ketoprofen, fenamates (mefenamic acid, meclofenamic acid), enolic acids (piroxicam, meloxicam), nabumetone, celecoxib, etodolac, nimesulide, apazone, gold, sulindac or tepoxalin; antioxidants, such as dithiocarbamate, and other compounds such as sulfasalazine [2-hydroxy-5-[-4-[C2-pyridinylamino)sulfonyl]azo]benzoic acid], steroids, such as fluocinolone, cortisol, cortisone, hydrocortisone, fludrocortisone, prednisone, prednisolone, methylprednisolone, triamcinolone, betamethasone, dexamethasone, beclomethasone, fluticasone, protein inhibitors of TNF, such as etanercept, Remicade, IL-1, such as Kineret®, p38, RANK, RANKL or a combination thereof.

The drug depot can comprise at least one analgesic agent or its pharmaceutically acceptable salt and/or at least one anti-inflammatory agent or its pharmaceutically acceptable salt and may be co-administered with a muscle relaxant. Co-administration may involve administering at the same time in separate drug depots or formulating together in the same drug depot.

Exemplary muscle relaxants include by way of example and not limitation, alcuronium chloride, atracurium bescylate, baclofen, carbolonium, carisoprodol, chlorphenesin carbamate, chlorzoxazone, cyclobenzaprine, dantrolene, decamethonium bromide, fazadinium, gallamine triethiodide, hexafluorenium, meladrazine, mephensin, metaxalone, methocarbamol, metocurine iodide, pancuronium, pridinol mesylate, styramate, suxamethonium, suxethonium, thiocolchicoside, tizanidine, tolperisone, tubocuarine, vecuronium, or combinations thereof.

The drug depot may also comprise other therapeutic agents or active ingredients in addition to the at least one chemonucleolysis agent, the at least one analgesic agent or its pharmaceutically acceptable salt or the at least one anti-inflammatory agent or its pharmaceutically acceptable salt. Suitable additional therapeutic agents include, but are not limited to, integrin antagonists, alpha-4 beta-7 integrin antagonists, cell adhesion inhibitors, interferon gamma antagonists, CTLA4-Ig agonists/antagonists (BMS-188667), CD40 ligand antagonists, Humanized anti-IL-6 mAb (MRA, Tocilizumab, Chugai), HMGB-1 mAb (Critical Therapeutics Inc.), anti-IL2R antibodies (daclizumab, basilicimab), ABX (anti IL-8 antibodies), recombinant human IL-10, or HuMax IL-15 (anti-IL 15 antibodies).

Other suitable therapeutic agents that may be co-administered or in the depot with the chemonucleolysis agent, anti-inflammatory agent or analgesic agent include IL-1 inhibitors, such Kineret® (anakinra) which is a recombinant, non-glycosylated form of the human inerleukin-1 receptor antagonist (IL-1Ra), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. It is contemplated that where desirable a pegylated form of the above may be used. Examples of other therapeutic agents include NF kappa B inhibitors such as glucocorticoids, antioxidants, such as dilhiocarbamate.

Specific examples of additional therapeutic agents suitable for use in the depot include, but are not limited to, an anabolic growth factor or anti-catabolic growth factor, analgesic agent, or an osteoinductive growth factor or a combination thereof.

Suitable anabolic growth or anti-catabolic growth factors include, but are not limited to, a bone morphogenetic protein, a growth differentiation factor, a LIM mineralization protein, CDMP or progenitor cells or a combination thereof.

For each of the chemonucleolysis agents, analgesic agents, anti-inflammatory agents and/or growth factor, in some embodiments, the release of each compound may be for at least one, at least two, at least three, at least four, at least five, at least six, at least seven, at least eight, at least nine, at least ten, at least eleven, at least twelve, at least thirteen, at least fourteen, or at least fifteen days, or 30 days, or 60 days or 90 days or longer.

The drug depot may also be administered with non-active ingredients. These non-active ingredients may have multi-functional purposes including the carrying, stabilizing and controlling the release of the therapeutic agent(s). The sustained release process, for example, may be by a solution-diffusion mechanism or it may be governed by an erosion-sustained process.

In various embodiments, the non-active ingredients will be durable within the tissue site for a period of time equal to (for biodegradable components) or greater than (for non-biodegradable components) the planned period of drug delivery. For example, the depot material may have a melting point or glass transition temperature close to or higher than body temperature, but lower than the decomposition or degradation temperature of the therapeutic agent. However, the pre-determined erosion of the depot material can also be used to provide for slow release of the loaded therapeutic agent(s).

In some instance, it may be desirable to avoid having to remove the drug depot after use. In those instances, the depot may comprise a biodegradable material. There are numerous materials available for this purpose and having the characteristic of being able to breakdown or disintegrate over a prolonged period of time when positioned at or near the target tissue. As a function of the chemistry of the biodegradable material, the mechanism of the degradation process can be hydrolytical or enzymatical in nature, or both. In various embodiments, the degradation of the drug depot can occur either at the surface (heterogeneous or surface erosion) or uniformly throughout the drug depot (homogeneous or bulk erosion).

In various embodiments, the depot may comprise a bioabsorbable, and/or a biodegradable biopolymer that may provide immediate release, or sustained release of the at least one chemonucleolysis agent, at least one analgesic agent, at least one anti-inflammatory agent, and/or at least one growth factor. Examples of suitable sustained release biopolymers include but are not limited to poly (alpha-hydroxy acids), poly (lactide-co-glycolide) (PLGA or PLG), polylactide (PLA), polyglycolide (PG), polyethylene glycol (PEG) conjugates of poly (alpha-hydroxy acids), polyorthoesters, poly (propylene fumarate), polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, D,L-lactide-ϵ-caprolactone, D,L-lactide-glycolide-ϵ-caprolactone, poly(glycolide-ϵ-caprolactone), ϵ-caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations or copolymers thereof. As persons of ordinary skill are aware, mPEG may be used as a plasticizer for PLGA, but other polymers/excipients may be used to achieve the same effect. mPEG imparts malleability to the resulting formulations.

Where different combinations of polymers are used (bi, tri (e.g., PLGA-PEO-PLGA) or terpolymers), they may be used in different molar ratios, 1:1, 2:1, 3:1, 4:1, 5:1, 6:1, 7:1, 8:1, 9:1, or 10:1. For example, for a 130-day release drug depot, the polymer make up is 50:50 PLGA to 100 PLA. The molecular weight range is 0.45 to 0.8 dI/g.

In various embodiments, the molecular weight of the polymer can be a wide range of values. The average molecular weight of the polymer can be from about 1000 to about 10,000,000; or about 1,000 to about 1,000,000; or about 5,000 to about 500,000; or about 10,000 to about 100,000; or about 20,000 to 50,000.

In some embodiments, the at least one biodegradable polymer comprises poly(lactic-co-glycolic acid) (PLA) or poly (orthoester) (POE) or a combination thereof. The poly(lactic-co-glycolic acid) may comprise a mixture of polyglycolide (PGA) and polylactide and in some embodiments, in the mixture, there is more polylactide than polyglycolide. In various other embodiments there is 100% polylactide and 0% polyglycolide; 95% polylactide and 5% polyglycolide; 90% polylactide and 10% polyglycolide; 85% polylactide and 15% polyglycolide; 80% polylactide and 20% polyglycolide; 75% polylactide and 25% polyglycolide; 70% polylactide and 30% polyglycolide; 65% polylactide and 35% polyglycolide; 60% polylactide and 40% polyglycolide; 55% polylactide and 45% polyglycolide; 50% polylactide and 50% polyglycolide; 45% polylactide and 55% polyglycolide; 40% polylactide and 60% polyglycolide; 35% polylactide and 65% polyglycolide; 30% polylactide and 70% polyglycolide; 25% polylactide and 75% polyglycolide; 20% polylactide and 80% polyglycolide; 15% polylactide and 85% polyglycolide; 10% polylactide and 90% polyglycolide; 5% polylactide and 95% polyglycolide; and 0% polylactide and 100% polyglycolide.

In various embodiments that comprise both polylactide and polyglycolide; there is at least 95% polylactide; at least 90% polylactide; at least 85% polylactide; at least 80% polylactide; at least 75% polylactide; at least 70% polylactide; at least 65% polylactide; at least 60% polylactide; at least 55%; at least 50% polylactide; at least 45% polylactide; at least 40% polylactide; at least 35% polylactide; at least 30% polylactide; at least 25% polylactide; at least 20% polylactide; at least 15% polylactide; at least 10% polylactide; or at least 5% polylactide; and the remainder of the biopolymer being polyglycolide.

In some embodiments, the biodegradable polymer comprises at least 10 wt %, at least 50 wt. %, at least 60 wt. %, at least 70 wt. %, at least 80 wt. %, at least 85 wt. %, at least 90 wt. %, at least 95 wt. %, or at least 99 wt. % of the formulation. In some embodiments, the at least one biodegradable polymer and the therapeutic agent are the only components of the pharmaceutical formulation that is used to make the depot.

In some embodiments, at least 75% of the particles in the depot have a size from about 1 micrometer to about 250 micrometers. In some embodiments, at least 85% of the particles have a size from about 1 micrometer to about 100 micrometers. In some embodiments, at least 95% of the particles have a size from about 1 micrometer to about 30 micrometers. In some embodiments, all of the particles have a size from about 1 micrometer to about 30 micrometers.

In some embodiments, at least 75% of the particles have a size from about 5 micrometer to about 20 micrometers. In some embodiments, at least 85% of the particles have a size from about 5 micrometers to about 20 micrometers. In some embodiments, at least 95% of the particles have a size from about 5 micrometer to about 20 micrometers. In some embodiments, all of the particles have a size from about 5 micrometer to about 20 micrometers.

The depot may optionally contain inactive materials such as buffering agents and pH adjusting agents such as potassium bicarbonate, potassium carbonate, potassium hydroxide, sodium acetate, sodium borate, sodium bicarbonate, sodium carbonate, sodium hydroxide or sodium phosphate; degradation/release modifiers; drug release adjusting agents; emulsifiers; preservatives such as benzalkonium chloride, chlorobutanol, phenylmercuric acetate and phenylmercuric nitrate, sodium bisulfite, sodium bisulfate, sodium thiosulfate, thimerosal, methylparaben, polyvinyl alcohol and phenylethyl alcohol; solubility adjusting agents; stabilizers; and/or cohesion modifiers. Typically, any such inactive materials will be present within the range of 0-75 wt %, and more typically within the range of 0-30 wt %. If the depot is to be placed in the spinal area, in various embodiments, the depot may comprise sterile preservative free material.

The depot can be different sizes, shapes and configurations, such as for example, strip, rod, sheet, mesh, pellet, microsphere, sphere, or the like. There are several factors that can be taken into consideration in determining the size, shape and configuration of the drug depot. For example, both the size and shape may allow for ease in positioning the drug depot at the target tissue site that is selected as the implantation site. In addition, the shape and size of the system should be selected so as to minimize or prevent the drug depot from moving after implantation or injection. In various embodiments, the drug depot can be shaped like a pellet, a sphere, a cylinder such as a rod, a flat surface such as a disc, film or sheet, strip, rod, mesh, or the like. Flexibility may be a consideration so as to facilitate placement of the drug depot. In various embodiments, the drug depot can be different sizes, for example, the drug depot may be a length of from about 2 to 4 cm and width of from about 1-2 cm and thickness of from about 0.25 to 1 mm, or length of from about 0.5 mm to 5 cm and have a diameter of from about 0.01 to about 2 mm. In various embodiments, the depot is a strip having dimensions of 2.5 cm×1.5 cm×0.5 mm. In various embodiments, the drug depot may have a layer thickness of from about 0.005 to 1.0 mm, such as, for example, from 0.05 to 0.75 mm.

In some embodiments, the drug depot (e.g., microspheres, nanospheres, pellets, etc.) can be mixed, stirred, agitated, injected, emulsified, molded, etc. into the formulation to provide a uniform distribution of the drug depot within the formulation. In alternative embodiments, the drug depot (e.g., microspheres, nanospheres, pellets, etc.) can be mixed, stirred, agitated, injected, molded, etc. in the formulation to provide a non-uniform distribution of the drug depot within the formulation in the center or at certain regions of it.

In some embodiments, the methods provided can be used to treat patients with mild to moderate disc degeneration and an essentially intact and competent annulus fibrosis. As explained herein, delivery of the chemonucleolysis agent may be accomplished with little or no additional injury to the annulus fibrosis. In some embodiments, the methods provided herein may be especially useful for patients that are not good candidates for nucleus replacement surgery, spinal fixation, total disc replacement, spinal fusion, and other surgical regimens for the treatment of degenerated intervertebral discs.

Accordingly, in some embodiments, there is a method for treating an intervertebral disc having a nucleus pulposus and an annulus fibrosis, the method comprising administering an implantable and biodegradable device to the nucleus pulposus, the device comprising a chemonucleolysis agent to proteolytically degrade at least a portion of the intervertebral disc and being configured to immediately release an effective amount of the chemonucleolysis agent within 24 hours and provide sustained release of the chemonucleolysis agent over a period of up to one year to treat the intervertebral disc. The intervertebral disc may be a cervical, lumbar, or thoracic disc.

In some embodiments, chemonucleolysis is used treat a disc before undergoing discectomy, to facilitate easier or more complete removal of disc tissue.

In some embodiments, the method utilizes an implantable and biodegradable device that is administered to the nucleus pulposus by inserting a needle or cannula into the annulus fibrosis such that the inserted end of the needle or cannula is inside the nucleus pulposus of the intervertebral disc; and the device is pushed into the nucleus pulposus of the intervertebral disc; and then the needle or cannula is removed.

In some embodiments, the method utilizes an implantable and biodegradable device that is a drug depot comprising a polymer and hyaluronidase to proteolytically degrade at least a portion of a nucleus pulposus of the intervertebral disc, the drug depot having an immediate release layer is configured to release an effective amount of the hyaluronidase within 24 hours and a sustained release layer contacting the immediate release layer to provide sustained release of the hyaluronidase over a period of up to 3 months to treat the intervertebral disc.

A skilled artisan will be capable of determining the desired amount of chemonucleolysis agent based on a number of factors, including, for example, the degree of disc degeneration, the age, weight, and health of the patient, and the degree of restoration required. Additionally, the methods provided herein may be used to slow the rate of progressive collapse of an intervertebral disc and/or maintain the height of an intervertebral disc experiencing progressive collapse.

The depot containing the chemonucleolysis agent can be incorporated in a syringe or cannula and delivered to the intervertebral disc. The depot containing the chemonucleolysis agent may be delivered to the disc space in a variety of forms, such as beads, fibers, flakes, granules, microspheres, nano-particles, particles, pellets, platelets, powder, randomly shaped particles, rods, chunks, pieces, and so forth.

In some embodiments, whatever form the drug depot is in, it may be delivered to the intervertebral disc space, for example, utilizing "dry" or "wet" delivery methods.

In the "wet" delivery method, the depot containing the chemonucleolysis agent may be fluidized, for example, by mixing the depot containing with a medium to form a gel, suspension, paste, solution, mixture, etc. of the chemonucleolysis agent that is sufficiently fluid to be delivered through a needle, catheter, trocar, cannula, syringe, caulk gun-like device, barrel-plunger device, other injection or extrusion devices, or any other such applicable delivery device. For example, the delivery device may be used to pierce or puncture the annulus fibrosis in order to reach the interior of the disc space and nucleus pulposus. If desired, a more rigid, larger diameter cannula may be used to gain access to the outer disc annulus, and a smaller diameter needle may be used to puncture the annulus and inject the drug depot into the disc space. Additionally, if desired, a more rigid instrument such as a stylet may be used to guide the delivery device through the body and towards the disc space.

In some embodiments, the drug depot may be introduced into the delivery device and subjected to pressure or mechanical forces in order to force the drug depot to exit the distal end of the delivery device and enter the intervertebral disc space. In an exemplary embodiment, a syringe filled with the drug depot in the form of a gel, suspension, paste, solution, mixture, etc. may be used to force the drug depot through the delivery device (e.g., a needle, cannula, catheter, trocar, etc.) and into the disc space, where the therapeutic agent will be released from the drug depot and will expand in the disc.

In some embodiments, the drug depot may be delivered to the disc space via a "dry" delivery method, without rendering the drug depot flowable. According to the dry delivery method, the drug depot may be packed into a small diameter delivery device such as a needle, catheter, trocar, cannula, etc. in the form of a dry powder, particulates, small chunks, pellets, short rods, chunks, pieces, and so forth. No fluid is mixed with the drug depot prior to delivery to the intervertebral disc space. In some embodiments, the delivery device has a diameter of no more than about 3 mm, 2 mm, or 1 mm.

In some embodiments, the annulus fibrosis may be punctured and the delivery device inserted. In some embodiments, the delivery device itself may be used to puncture the annulus fibrosis, especially when the delivery device is a needle or trocar. The distal end of the delivery device then may be brought close to the center of the disc space. A plunger, stylet, or other such device may be used to extrude or push the drug depot through the delivery device and into the disc space. When the one or more drug depots are delivered to the disc space, the delivery device may be removed.

Cannula or Needle

The chemonucleolysis agent can be loaded in a cannula or needle that is designed to cause minimal physical and psychological trauma to the patient. Cannulas or needles include tubes that may be made from materials, such as for example, polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. The cannula or needle may optionally include one or more tapered regions. In various embodiments, the cannula or needle may be beveled. The cannula or needle may also have a tip style vital for accurate treatment of the patient depending on the site for implantation. Examples of tip styles include, for example, Trephine, Cournand, Veress, Huber, Seldinger, Chiba, Francine, Bias, Crawford, deflected tips, Hustead, Lancet, or Tuohey. In various embodiments, the cannula or needle may also be non-coring and have a sheath covering it to avoid unwanted needle sticks.

The dimensions of the hollow cannula or needle, among other things, will depend on the site for implantation. For example, the width of the epidural space is only about 3-5 mm for the thoracic region and about 5-7 mm for the lumbar region. Thus, the needle or cannula, in various embodiments, can be designed for these specific areas. Some examples of lengths of the cannula or needle may include, but are not limited to, from about 50 to 150 mm in length, for example, about 65 mm for epidural pediatric use, about 85 mm for a standard adult and about 150 mm for an obese adult patient. The thickness of the cannula or needle will also depend on the site of implantation. In various embodiments, the thickness includes, but is not limited to, from about 0.05 to about 1.655. The gauge of the cannula or needle may be the widest or smallest diameter or a diameter in between for insertion into a human or animal body. The widest diameter is typically about 14 gauge, while the smallest diameter is about 25 gauge. In various embodiments the gauge of the needle or cannula is about 17 to about 25 gauge.

In various embodiments, the plunger, cannula, and/or drug depot can include markings that indicate location at or near the site beneath the skin. Radiographic markers can be included to permit the user to accurately position the needle or cannula, or drug depot into the site of the patient. These radiographic markers will also permit the user to track movement and degradation of the drug depot at the site over time. In this embodiment, the user may accurately position the drug depot in the site using any of the numerous diagnostic-imaging procedures. Such diagnostic imaging procedures include, for example, X-ray imaging or fluoroscopy. Examples of such radiographic markers include, but are not limited to, barium, calcium phosphate, and/or metal beads.

In various embodiments, the needle or cannula may include a transparent or translucent portion that can be visualizable by ultrasound, fluoroscopy, x-ray, or other imaging techniques. In such embodiments, the transparent or translucent portion may include a radiopaque material or ultrasound responsive topography that increases the contrast of the needle or cannula relative to the absence of the material or topography. The drug depot may be administered in conjunction with a standard discogram.

In one embodiment, the delivery system for the drug depot can include any syringe based system that would be used to administer a discogram. These syringe based systems include inflation syringes with a fine and coarse drive, in conjunction with a pressure gage.

In one embodiment, the drug depot can be administered to the disc using a Kyphon Discyphor catheter system available from Medtronic Spine LLC in Sunnyvale, Calif., USA, where the damaged disc can be diagnosed and treated using the same catheter. Thus, the drug depot can be delivered to the disc in one procedure using the same catheter system.

Administration

In various embodiments, a device (e.g., drug depot) is administered locally to an intervertebral disc. In various embodiments, the drug depot can be parenterally administered. The term "parenteral" as used herein refers to modes of administration, which bypass the gastrointestinal tract, and include for example, intramuscular, intraperitoneal, intrasternal, subcutaneous, intra-operatively, intrathecally, intradiskally, peridiskally, epidurally, perispinally, intraarticular or combinations thereof. Administration may be performed while the patient is at rest or in a distracted position, while standing, laying or sitting.

In various embodiments, because the drug depot is locally administered, therapeutically effective doses may be less than doses administered by other routes (oral, topical, etc.). In turn, systemic side effects, such as for example, liver transaminase elevations, hepatitis, liver failure, myopathy, constipation, etc. may be reduced or eliminated. Because the drug depot is administered locally the patient receives treatment at the appropriate site and separate introductions of therapeutic agents are not needed.

The drug depot can be delivered to any site beneath the skin, including, but not limited to, at least one muscle, ligament, tendon, cartilage, spinal disc, spinal foraminal space, intrathecal space, near the spinal nerve root, or spinal canal.

Referring to FIG. 1, the reference numeral 10 refers to a vertebral joint section or a motion segment of a vertebral column. The joint section 10 includes adjacent vertebral bodies 12 and 14. The vertebral bodies 12 and 14 include endplates 16 and 18, respectively. An intervertebral disc space 20 is located between the endplates 16, and 18, and an annulus fibrosis 22 surrounds the space 20 and holds a nucleus pulposus 24.

Figure 2:
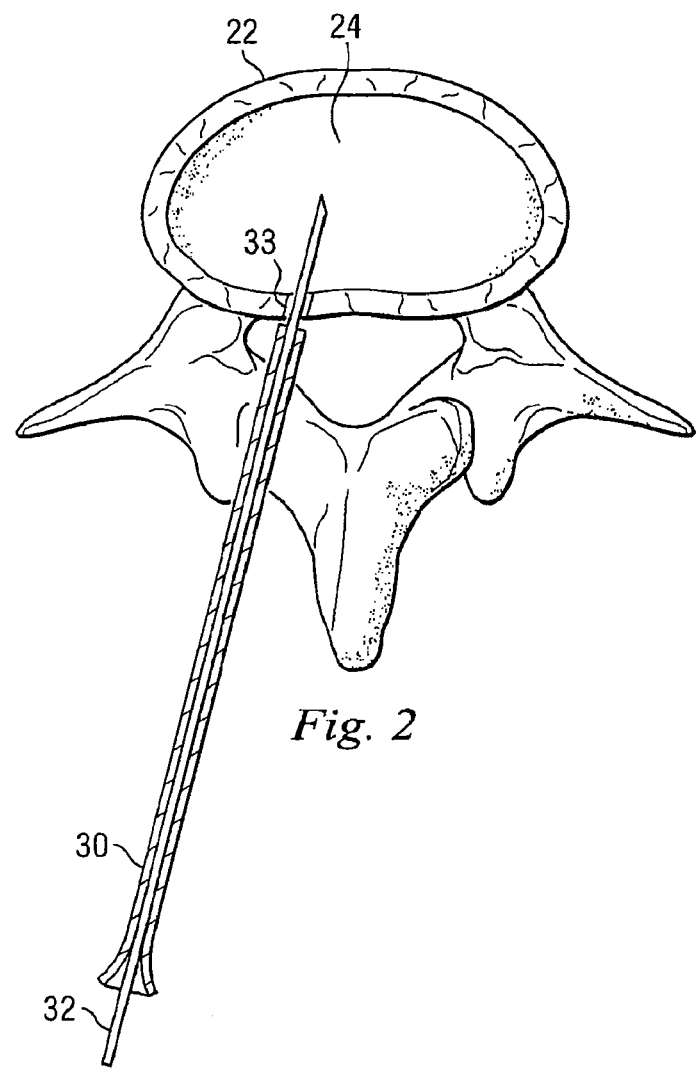
FIG. 2 illustrates an embodiment of an intervertebral disc treatment including inserting a cannula or needle into the annulus fibrosis and into the nucleus pulposus of the intervertebral disc so that the device can be administered thereto.

Referring now to FIG. 2, in this embodiment, an annular tear 33 is present that nucleus pulposus 24 can herniate out of this tear. In the embodiments of the present application, a chemonucleolysis agent in a device (e.g. drug depot) is to be delivered through the annulus fibrosis of the disc by inserting a sheath 30 into the patient and locating the cannula 32 through the sheath 30 and through annular tear 33 and delivering the drug depot containing the chemonucleolysis agent to the nucleus pulposus 24. The chemonucleolysis agent can be delivered by coupling a syringe containing this agent to cannula 32. The chemonucleolysis agent will be released from the drug depot, which will degrade or cause the dissolution or shrinkage of a portion of the nucleus pulposus and/or an annulus fibrosus or other tissue in or surrounding the intervertebral disc, which reduces intervertebral disc pressure and pain and/or inflammation associated therewith and, in some embodiments, allows retraction of herniated tissue. The drug depot is configured to immediately release the chemonucleolysis agent within seconds or minutes to within 24 hours so that the chemonucleolysis agent begins to exert its effect and the drug depot is also configured to provide sustained release of the chemonucleolysis agent as the drug depot degrades, where it will release the chemonucleolysis agent into the nucleus pulposus for extended periods of time. In this way, the chemonucleolysis agent will stay locally at the target tissue site and will provide treatment of the intervertebral disc for an extended period of time. Thus, one catheter can be used to deliver an "all-in-one composition".

Figure 3:
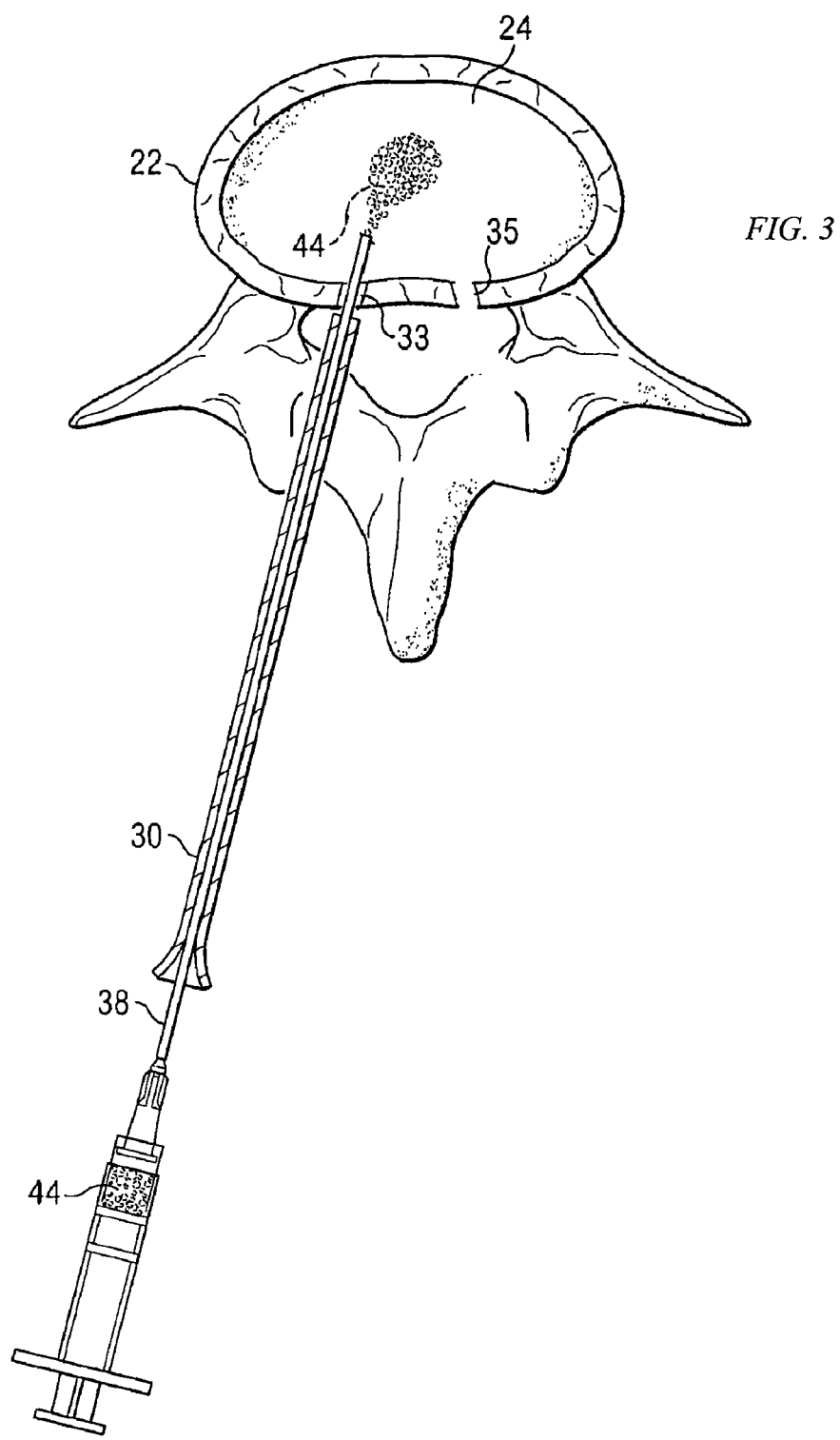
FIG. 3 illustrates an embodiment of an intervertebral disc treatment including administering a biodegradable device shown as a plurality of drug depots containing a chemonucleolysis agent into the nucleus pulposus of the intervertebral disc.

Referring now to FIG. 3, in this embodiment, an annular tear 35 is present and some of the nucleus pulposus 24 has left the disc space from this tear as the disc is herniated. In the embodiment of the present application, a plurality of drug depots 44 (e.g., powder, microspheres, etc.) containing one or more chemonucleolysis agents are delivered to the nucleus pulposus 24 by introducing a sheath 30 into the annulus fibrosis 22 by making a hole 33 in the annulus fibrosis next to the annular tear 35 and inserting a catheter 38 where sheath 30 guides the catheter. The drug depots 44 containing the chemonucleolysis agent are delivered through the catheter 38 out the distal end of the cannula into the nucleus pulposus 24. The chemonucleolysis agent will be released from the drug depot, which will degrade or cause the dissolution or shrinkage of a portion of the nucleus pulposus or other tissue in or surrounding the intervertebral disc, which reduces intervertebral disc pressure and pain and/or inflammation associated therewith and, in some embodiments, allows retraction of herniated tissue. In this way the intervertebral disc is treated. In some embodiments, the drug depots will polymerize and/or cure in situ, alternatively, they can be administered in solid or semi-solid form. In some embodiments, the drug depots may also contain one or more additional therapeutic agents including a growth factor, an analgesic, an anti-inflammatory agent or a combination thereof.

In some embodiments, the nucleus is accessed using a posterior unilateral, bilateral or multi-lateral approach. In alternative embodiments, the annulus may be accessed with a lateral approach, an anterior approach, a trans-pedicular/vertebral endplate approach, an axial approach, or any other suitable nucleus accessing approach.

Figure 4:
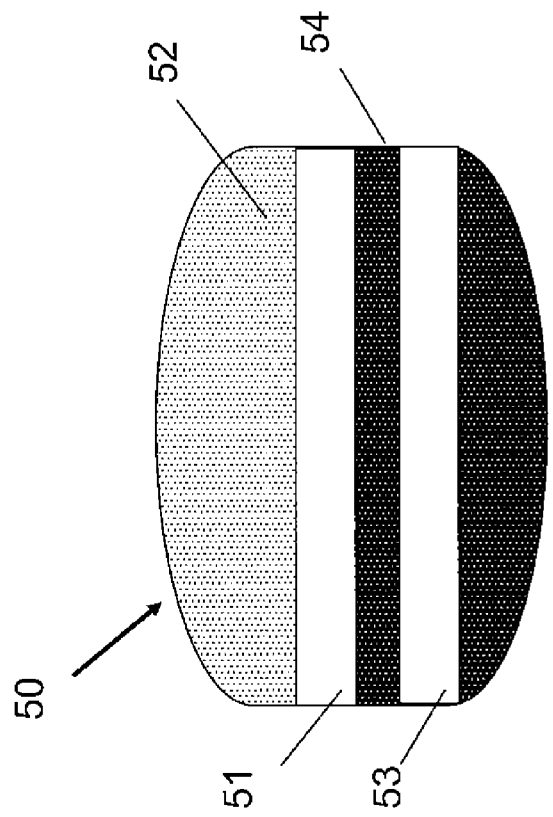
FIG. 4 illustrates an enlarged view of a drug depot containing an immediate release layer that immediately releases a chemonucleolysis agent and a sustained release layer that releases the chemonucleolysis agent over a prolonged period of time.

FIG. 4 illustrates an enlarged view of a solid or semi-solid drug depot 50 containing an immediate release layer 52 that immediately releases a chemonucleolysis agent as soon as it is implanted within 24 hours and, as the layer degrades, a sustained release layer 54 releases the chemonucleolysis agent over a prolonged period of time (e.g., about 3 days to about 3 months or longer).

Alternatively, the drug depots can be designed with regions that provide immediate release of the same or different therapeutic agent and regions that provide sustain release of the same or different therapeutic agent.

In some embodiments, the drug depot may have one or more additional therapeutic agents disposed in one or more regions that can provide immediate or sustain release of the therapeutic agent. For example, a growth factor, an analgesic, an anti-inflammatory agent or a combination thereof can be disposed in layer 51 and can be released either in an immediate release or a sustained release fashion after the immediate release layer comprising the chemonucleolysis agent is released.

In the embodiment shown, the additional therapeutic layer 51 is separate from the immediate release layer 52 and can comprise an anti-inflammatory agent or analgesic that can be in an immediate release formulation to provide immediate relief of pain and/or inflammation locally at the site of implantation. After the additional therapeutic agent is released, a sustained release layer 54 containing the chemonucleolysis agent can release the chemonucleolysis agent over an extended period of time. After this layer degrades, an additional therapeutic agent shown as layer 53, such as for example, a growth factor is kept separate from the sustained release layer 54 containing the chemonucleolysis agent. This is because, in some embodiments, the chemonucleolysis agent, which is often an enzyme, can degrade the growth factor. By keeping the growth factor and the chemonucleolysis agent in a separate layer, premature degradation of the growth factor and/or chemonucleolysis agent and loss in potency is reduced. After the growth factor 53 is released from the depot and as the layer degrades, the sustained release layer can degrade and continue to release the chemonucleolysis agent over a prolonged period of time.

Although the drug depot 50 is shown as a five layered depot, it will be understood by one of ordinary skill in the art that the depot can have the chemonucleolysis agent and additional therapeutic agent disposed in the same or different layers in immediate release or sustained release formulations. In some embodiments, the drug depot can have an immediate release portion and a sustained release portion disposed uniformly distributed through one or more layers of the depot containing the chemonucleolysis agent alone or in combination with the additional therapeutic agent. In some embodiments, the drug depot can have one, two, three, four, five, six, seven, eight, nine, ten or more layers, where each layer can contain one or more therapeutic agents that can be in an immediate release formulation, sustained release formulation or a combination thereof. A multi-layered or multi-region depot is shown in FIG. 4.

Figure 5:
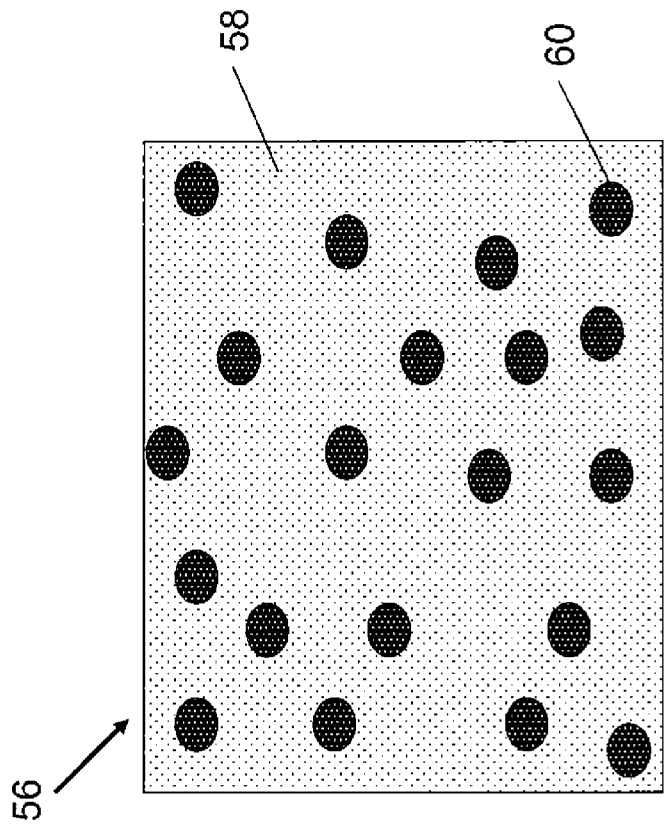
FIG. 5 illustrates an enlarged view of an embodiment of a drug depot containing an immediate release portion that immediately releases a chemonucleolysis agent and a sustained release portion in microspheres that releases the chemonucleolysis agent over a prolonged period of time.

FIG. 5 illustrates an enlarged view of a drug depot 56 containing an immediate release region 58 which is in liquid, semi-solid or solid form that immediately releases a chemonucleolysis agent as soon as it is implanted within 24 hours and, as the region degrades, a sustained release microspheres (one shown as 60) releases the chemonucleolysis agent over a prolonged period of time (e.g., about 3 days to about 3 months or longer).

In some embodiments, the drug depot may have one or more additional therapeutic agents disposed in one or more regions that can provide immediate or sustained release of the therapeutic agent. For example, a growth factor, an analgesic, an anti-inflammatory agent or a combination thereof can be disposed in region 58 or microsphere 60 and be released either in an immediate release or a sustained release fashion as the drug depot 56 degrades.

Although the drug depot 56 is shown as a square shape, it will be understood by one of ordinary skill in the art that the depot can be any shape or it can be amorphous and cure or harden as a depot or it can be a plurality of depots containing the chemonucleolysis agent in a sustained release formulation. In some embodiments, the drug depots can be uniformly disposed through out the formulation or it can be concentrated in one area of the formulation. In some embodiments, the drug depot will expand and polymerize and/or cure in situ to fill the space in the nucleus pulposus 24.

The techniques and devices described herein provide a safe and effective means for various types of disc treatment including, but not limited to, chemonucleolysis, pain-management, repair, and regeneration. These techniques and devices also allow for the controlled and/or sustained release of desirable active agents within the disc. Further, the techniques and devices described herein can deliver an active agent to a localized area of the disc. For example, an implant comprising a chemonucleolysis agent such as hyaluronidase can be used to achieve localized degradation of the nucleus of an intervertebral disc without the destruction of other disc tissues including the annulus fibrosus. In this manner, reductions in the intradiscal pressure can be achieved using an implant comprising a chemonucleolysis agent. The above mentioned techniques and devices can also be used to avoid the potential side effects associated with the direct injection of a solution of an active agent including leakage or overdose. Therefore, the techniques and devices described herein can result in prolonged therapeutic effects while minimizing these and other adverse/side effects.

In some embodiments, the therapeutically effective dosage amount (e.g., chemonucleolysis agent, analgesic, anti-inflammatory agent, and/or growth factor, etc.) and the release rate profile of the therapeutic agent is sufficient to reduce inflammation and/or pain for a period of at least one day, for example, 1-90 days, 1-10 days, 1-3 days, 3-7 days, 3-12 days; 3-14 days, 3-25 days, 3-45 days, 7-10 days, 7-14 days, 7-21 days, 7-30 days, 7-50 days, 7-90 days, 7-140 days, or 14-140 days, 3 days-3 months, 7 days to 6 months, 10 days to 1 year.

In some embodiments, the therapeutic agent is released from the depot as a bolus dose at the target tissue to provide an immediate release of the therapeutic agent.

In some embodiments, there is a composition useful for the treatment of pain and/or inflammation associated with an intervertebral disc comprising an effective amount of at least one chemonucleolysis agent alone or in combination with at least one analgesic agent, at least one anti-inflammatory agent, and/or at least one growth factor that is capable of being administered to a target tissue site e.g., a pain or inflammatory site. By way of example, they may be administered locally to one or more intervertebral discs.

In some embodiments, a plurality of depots containing the chemonucleolysis agent, analgesic, anti-inflammatory agent, and/or growth factor can be placed in and around the disc to provide a strategy to triangulate around the pain generator. A strategy of triangulation may be effective when administering multiple depot pharmaceutical formulations. Thus, a plurality (at least two, at least three, at least four, at least five, at least six, at least seven, etc.) drug depots may be placed around the target tissue site (also known as the pain generator or pain generation site) such that the target tissue site falls within a region that is either between the formulations when there are two, or within an area whose perimeter is defined by a set of plurality of formulations. Alternatively repeat administration to lengthen the delivery timeframe may be required.

In some embodiments, a desired release rate profile is maintained for at least three days, at least ten days, at least twenty days, at least thirty days, at least forty days, at least fifty days, at least ninety days, at least one hundred days, at least one-hundred and thirty-five days, at least one-hundred and fifty days, or at least one hundred and eighty days, or at least 1 year.

In some embodiments, the drug depot may release 5%, 10%, 15%, 20%, 25%, 30%, 40%, 50%, 60%, 70%, 80%, 90%, 95%, or 99% of the therapeutic agent (e.g., chemonucleolysis agent) or pharmaceutically acceptable salt thereof relative to a total amount of the therapeutic agent loaded in the drug depot over a period of at least three days, at least seven days, at least ten days, at least twenty days, at least thirty days, at least forty days, at least fifty days, at least ninety days, at least one hundred days, at least one-hundred and thirty-five days, at least one-hundred and fifty days, or at least one hundred and eighty days, or at least 1 year.

In various embodiments, the chemonucleolysis agent, analgesic, anti-inflammatory agent, and/or growth factor will be released in an initial burst dose, then one or more of these therapeutic agents will be released daily for 3 days and then stop (e.g., this will be suitable to reduce, prevent or treat, acute pain), while the chemonucleolysis agent, analgesic, anti-inflammatory agent, and/or growth factor will be released daily without a burst dose for 3 to 12 days, 5 to 10 days or 7 to 10 days or longer after the drug depot is administered to the target tissue site.

In various embodiments, a kit is provided comprising one or more drug depots containing one or more chemonucleolysis agents, analgesics, anti-inflammatory agents, and/or growth factors. The kit may also include additional parts along with the drug depots combined together to be used to administer it. The kit may include the drug depot and delivery device in a first compartment. The second compartment may include a canister holding the drug depots and any other instruments needed for the localized drug delivery. A third compartment may include gloves, drapes, needles, wound dressings and other procedural supplies for maintaining sterility of the implanting process, as well as an instruction booklet. A fourth compartment may include additional needles and/or sutures. Each tool may be separately packaged in a plastic pouch that is radiation sterilized. A fifth compartment may include an agent for radiographic imaging. A cover of the kit may include illustrations of the implanting procedure and a clear plastic cover may be placed over the compartments to maintain sterility.

The devices and methods of the present application can be used to treat spinal arachnoiditis. Spinal arachnoiditis is a pain disorder caused by the inflammation of the arachnoid, one of the membranes that surround and protect the nerves of the spinal cord. It is characterized by severe stinging, "burning pain," and neurological problems.

Spinal arachnoiditis has no consistent pattern of symptoms, but in many people it affects the nerves connecting to the lower back and legs. In spinal arachnoiditis, the inflammation can cause fibrosis (e.g., scarring) and adhesions of the arachnoid, nerve roots, and blood vessels. By implanting the device containing the chemonucleolysis agent in or near the intrathecal space and/or thecal sac, the chemonucleolysis agent can degrade the fibrous tissue and release adhesions and, therefore, the spinal arachnoiditis can be treated.

The devices and methods of the present application can be used to treat sciatica. In general, sciatica refers to pain associated with the sciatic nerve which runs from the lower part of the spinal cord (the lumbar region), down the back of the leg and to the foot. Sciatica generally begins with a herniated disc. The herniated disc itself leads to local immune system activation. The herniated disc also may damage the nerve root by pinching or compressing it, leading to additional immune system activation in the area. By implanting the device containing the chemonucleolysis agent in the intervertebral disc or near a nerve root sciatica can be treated.

In some embodiments, the biodegradable depot is implanted intrathecally for treatment of arachnoiditis.

Method of Making Drug Depots

In various embodiments, the drug depot comprising the active ingredients (e.g., the chemonucleolysis agent, analgesic, anti-inflammatory agent, and/or growth factor) can be made by combining a biocompatible polymer and a therapeutically effective amount of the active ingredients or pharmaceutically acceptable salts thereof and forming the drug depot from the combination.

Where solution processing techniques are used to make the drug depot, a solvent system is typically selected that contains one or more solvent species. The solvent system is generally a good solvent for at least one component of interest, for example, biocompatible polymer and/or therapeutic agent. The particular solvent species that make up the solvent system can also be selected based on other characteristics, including drying rate and surface tension.

Solution processing techniques include solvent casting techniques, spin coating techniques, web coating techniques, solvent spraying techniques, dipping techniques, techniques involving coating via mechanical suspension, including air suspension (e.g., fluidized coating), ink jet techniques and electrostatic techniques. Where appropriate, techniques such as those listed above can be repeated or combined to build up the depot to obtain the desired release rate and desired thickness.

In various embodiments, a solution containing solvent and biocompatible polymer are combined and placed in a mold of the desired size and shape. In this way, polymeric regions, including barrier layers, lubricious layers, and so forth can be formed. If desired, the solution can further comprise, one or more of the following: other therapeutic agent(s) and other optional additives such as radiographic agent(s), etc. in dissolved or dispersed form. This results in a polymeric matrix region containing these species after solvent removal. In other embodiments, a solution containing solvent with dissolved or dispersed therapeutic agent is applied to a pre-existing polymeric region, which can be formed using a variety of techniques including solution processing and thermoplastic processing techniques, whereupon the therapeutic agent is imbibed into the polymeric region.

Thermoplastic processing techniques for forming the depot or portions thereof include molding techniques (for example, injection molding, rotational molding, and so forth), extrusion techniques (for example, extrusion, co-extrusion, multi-layer extrusion, and so forth) and casting.

Thermoplastic processing in accordance with various embodiments comprises mixing or compounding, in one or more stages, the biocompatible polymer(s) and one or more of the following: the active ingredients, optional additional therapeutic agent(s), radiographic agent(s), and so forth. The resulting mixture is then shaped into an implantable drug depot. The mixing and shaping operations may be performed using any of the conventional devices known in the art for such purposes.

During thermoplastic processing, there exists the potential for the therapeutic agent(s) to degrade, for example, due to elevated temperatures and/or mechanical shear that are associated with such processing. For example, certain therapeutic agents may undergo substantial degradation under ordinary thermoplastic processing conditions. Hence, processing is preferably performed under modified conditions, which prevent the substantial degradation of the therapeutic agent(s). Although it is understood that some degradation may be unavoidable during thermoplastic processing, degradation is generally limited to 10% or less. Among the processing conditions that may be controlled during processing to avoid substantial degradation of the therapeutic agent(s) are temperature, applied shear rate, applied shear stress, residence time of the mixture containing the therapeutic agent (e.g., the chemonucleolysis agent, analgesic, anti-inflammatory agent, and/or growth factor), and the technique by which the polymeric material and the therapeutic agent(s) are mixed.

Mixing or compounding biocompatible polymer with therapeutic agent(s) and any additional additives to form a substantially homogenous mixture thereof may be performed with any device known in the art and conventionally used for mixing polymeric materials with additives.

Where thermoplastic materials are employed, a polymer melt may be formed by heating the biocompatible polymer, which can be mixed with various additives (e.g., therapeutic agent(s), inactive ingredients, etc.) to form a mixture. A common way of doing so is to apply mechanical shear to a mixture of the biocompatible polymer(s) and additive(s). Devices in which the biocompatible polymer(s) and additive(s) may be mixed in this fashion include devices such as single screw extruders, twin screw extruders, banbury mixers, high-speed mixers, ross kettles, and so forth.

Any of the biocompatible polymer(s) and various additives may be premixed prior to a final thermoplastic mixing and shaping process, if desired (e.g., to prevent substantial degradation of the therapeutic agent among other reasons).

For example, in various embodiments, a biocompatible polymer is precompounded with a radiographic agent (e.g., radio-opacifying agent) under conditions of temperature and mechanical shear that would result in substantial degradation of the therapeutic agent, if it were present. This precompounded material is then mixed with the therapeutic agent under conditions of lower temperature and mechanical shear, and the resulting mixture is shaped into the active ingredient containing drug depot. Conversely, in another embodiment, the biocompatible polymer can be precompounded with the therapeutic agent under conditions of reduced temperature and mechanical shear. This precompounded material is then mixed with, for example, a radio-opacifying agent, also under conditions of reduced temperature and mechanical shear, and the resulting mixture is shaped into the drug depot.

The conditions used to achieve a mixture of the biocompatible polymer and therapeutic agent and other additives will depend on a number of factors including, for example, the specific biocompatible polymer(s) and additive(s) used, as well as the type of mixing device used.

As an example, different biocompatible polymers will typically soften to facilitate mixing at different temperatures. For instance, where a depot is formed comprising PLGA or PLA polymer, a radio-opacifying agent (e.g., bismuth subcarbonate), and a therapeutic agent prone to degradation by heat and/or mechanical shear (e.g., hyaluronidase), in various embodiments, the PGLA or PLA can be premixed with the radio-opacifying agent at temperatures of about, for example, 150° C. to 170° C. The therapeutic agent is then combined with the premixed composition and subjected to further thermoplastic processing at conditions of temperature and mechanical shear that are substantially lower than is typical for PGLA or PLA compositions. For example, where extruders are used, barrel temperature, volumetric output are typically controlled to limit the shear and therefore to prevent substantial degradation of the therapeutic agent(s). For instance, the therapeutic agent and premixed composition can be mixed/compounded using a twin screw extruder at substantially lower temperatures (e.g., room temperature), and using substantially reduced volumetric output (e.g., less than 30% of full capacity, which generally corresponds to a volumetric output of less than 200 cc/min). It is noted that this processing temperature is well below the melting points of certain active ingredients, such as an anti-inflammatory and analgesic because processing at or above these temperatures may result in substantial therapeutic agent degradation. It is further noted that in certain embodiments, the processing temperature will be below the melting point of all bioactive compounds within the composition, including the therapeutic agent. After compounding, the resulting depot is shaped into the desired form, also under conditions of reduced temperature and shear.

In other embodiments, biodegradable polymer(s) and one or more therapeutic agents are premixed using non-thermoplastic techniques. For example, the biocompatible polymer can be dissolved in a solvent system containing one or more solvent species. Any desired agents (for example, a radio-opacifying agent, a therapeutic agent, or both radio-opacifying agent and therapeutic agent) can also be dissolved or dispersed in the solvents system. Solvent is then removed from the resulting solution/dispersion, forming a solid material. The resulting solid material can then be granulated for further thermoplastic processing (for example, extrusion) if desired.

As another example, the therapeutic agent can be dissolved or dispersed in a solvent system, which is then applied to a pre-existing drug depot (the pre-existing drug depot can be formed using a variety of techniques including solution and thermoplastic processing techniques, and it can comprise a variety of additives including a radio-opacifying agent and/or viscosity enhancing agent), whereupon the therapeutic agent is imbibed on or in the drug depot. As above, the resulting solid material can then be granulated for further processing, if desired.

Typically, an extrusion processes may be used to form the drug depot comprising a biocompatible polymer(s), therapeutic agent(s) and radio-opacifying agent(s). Co-extrusion may also be employed, which is a shaping process that can be used to produce a drug depot comprising the same or different layers or regions (for example, a structure comprising one or more polymeric matrix layers or regions that have permeability to fluids to allow immediate and/or sustained drug release). Multi-region depots can also be formed by other processing and shaping techniques such as co-injection or sequential injection molding technology.

In various embodiments, the depot that may emerge from the thermoplastic processing (e.g., pellet, strip, etc.) is cooled.

Examples of cooling processes include air cooling and/or immersion in a cooling bath. In some embodiments, a water bath is used to cool the extruded depot. However, where water-soluble therapeutic agents are used, the immersion time should be held to a minimum to avoid unnecessary loss of therapeutic agent into the bath.

In various embodiments, immediate removal of water or moisture by use of ambient or warm air jets after exiting the bath will also prevent re-crystallization of the drug on the depot surface, thus controlling or minimizing a high drug dose "initial burst" or "bolus dose" upon implantation or insertion if this release profile is not desired. Thus, a sustained release region of the drug depot may, in various embodiments, be made by immediate removal of water or moisture.

In various embodiments, the drug depot can be prepared by mixing or spraying the drug with the polymer and then molding the depot to the desired shape. In various embodiments, active ingredients are used and mixed or sprayed with the PLGA or PEG550 polymer, and the resulting depot may be formed by extrusion and dried.

The drug depot may also comprise combining a biocompatible polymer and a therapeutically effective amount of at least chemonucleolysis agent, analgesic, anti-inflammatory agent, and/or growth factor or pharmaceutically acceptable salt thereof and forming the implantable drug depot from the combination.

In some embodiments, the therapeutic agent can be incorporated into a depot in the form of microspheres, nanospheres, etc. Examples of apparatus and aseptic procedures useful for the formation of sterile microspheres are described, e.g., in U.S. Pat. Nos. 5,945,126; 6,270,802; and 6,361,798, the disclosures of which are hereby incorporated by reference. These microspheres can then be dispersed or mixed and formed into the drug depot.

Microspheres can be made by a number of techniques, such as single and double emulsion, suspension polymerization, solvent evaporation, spray drying, and solvent extraction. Methods for making microspheres are described in the literature, for example, in Mathiowitz and Langer, J. Controlled Release 5:13-22 (1987); Mathiowitz et al., Reactive Polymers 6:275-283 (1987); Mathiowitz et al., J. Appl. Polymer Sci. 35:755-774 (1988); Mathiowitz et al., Scanning Microscopy 4:329-340 (1990); Mathiowitz et al., J. Appl. Polymer Sci., 45:125-134 (1992); and Benita et al., J. Pharm. Sci. 73:1721-1724 (1984).

In solvent evaporation, described for example in Mathiowitz et al., (1990), Benita et al. (1984), and U.S. Pat. No. 4,272,398, the macromers are dissolved in a solvent. If desired, an agent to be incorporated, either in soluble form or dispersed as fine particles, is added to the macromer solution, and the mixture is suspended in an aqueous phase that contains a surface active agent. The resulting emulsion is stirred until most of the solvent evaporates, leaving solid microspheres, which may be washed with water and dried overnight in a lyophilizer. The microspheres are polymerized, for example, by exposure to light.

In solvent removal, the macromers are dissolved in a solvent. The mixture can then be suspended in oil, such as silicon oil, by stirring, to form an emulsion. As the solvent diffuses into the oil phase, the emulsion droplets harden into solid polymer microspheres. The microspheres can be polymerized by exposure to light, for example.

Spray drying is implemented by passing the polymerizable macromers through a nozzle, spinning disk or equivalent device to atomize the mixture to form fine droplets. The polymerizable macromers may be provided in a solution or suspension, such as an aqueous solution. The fine droplets are exposed to light, for example, to cause polymerization of the macromer and formation of the microspheres.

In another embodiment, microspheres are prepared by a water-in-oil emulsion or suspension process, wherein the polymerizable macromers and the substance to be incorporated, if desired, are suspended in a water-in-oil suspension and exposed to light to polymerize the macromers to form particles incorporating the substance, such as the therapeutic agent.

In another embodiment, microspheres can be formed by atomizing macromer solution into oil, followed by polymerization.

In some embodiments, the drug depots are loaded into the formulation and are disposed uniformly throughout it or in a particular region (e.g., center or borders) and delivered in, at, or near the intervertebral disc. The drug depot will degrade and release the therapeutic agent at, near or in the intervertebral disc (e.g., nucleus pulposus, annulus fibrosis). For example, the drug depot will begin releasing the chemonucleolysis agent immediately or in a sustained release fashion to degrade the nucleus pulposus of the intervertebral disc.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A device for treating an intervertebral disc in a patient in need of such treatment, the device being biodegradable and implantable near or within the intervertebral disc, the device comprising
    a sustained release component having a chemonucleolysis agent, the sustained release component configured to provide sustained release of the chemonucleolysis agent over a period of up to one year to degrade or to shrink at least a portion of the intervertebral disc;
    an immediate release component having the chemonucleolysis agent, the immediate release component configured to immediately release an effective amount of the chemonucleolysis agent within 24 hours, the immediate release component comprising trehalose; and
    a therapeutic layer separate from the immediate release component and the sustained release component and configured to release at least one of a growth factor, an analgesic, and an anti-inflammatory agent in a bolus dose upon implantation near or within the intervertebral disc, wherein the chemonucleolysis agent comprises a polycationic polymer that dehydrates a nucleus pulposus of the intervertebral disc and the device comprises a pore forming agent.

2. A device according to claim 1, wherein the device comprises a drug depot that releases the chemonucleolysis agent over a period of at least 3 days to 3 months to degrade a nucleus pulposus of the intervertebral disc.

3. A device according to claim 2, wherein the immediate release component releases the chemonucleolysis agent within 24 hours and the sustained release component releases the chemonucleolysis agent over a period of at least 3 days to 3 months after implantation.

4. A device according to claim 2, wherein the drug depot comprises a polymer and the polymer comprises about 60% to 99% of the total weight % of the drug depot and the intervertebral disc is a herniated disc.

5. A device according to claim 1, wherein the device is a drug depot that releases (i) a bolus dose of the chemonucleolysis agent within the intervertebral disc over a period of up to 3 days and (ii) a sustained release dose of the chemonucleolysis agent within the intervertebral disc over a period of up to 3 months.

6. A device according to claim 1, wherein the device releases about 20% to about 99% of the chemonucleolysis agent relative to a total amount of the chemonucleolysis agent loaded in the device over a period of 3 days to at least 180 days after the device is administered within the intervertebral disc.

7. A device according to claim 1, wherein the chemonucleolysis agent comprises hyaluronidase in an amount of 0.05 mg - 0.8 mg per kg of the patient.

8. A device according to claim 2, wherein the drug depot comprises at least one biodegradable polymer comprising one or more of poly(lactide-co-glycolide) (PLGA), polylactide (PLA), polyglycolide (PGA), D-lactide, D,L-lactide, L-lactide, D,L-lactide-co-e-caprolactone, D,L-lactide-coglycolide-co-e-caprolactone or a combination thereof.

9. A device according to claim 2, wherein the drug depot is polymerizable in-situ or curable in-situ in the intervertebral disc.

10. A device according to claim 1, wherein the patient suffers from sciatica, spinal arachnoiditis, and/or a herniated disc.

11. A device according to claim 1, wherein the immediate release component release 51%, 52%, 53%, 54%, 55% 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% of the chemonucleolysis agent within the first one to twelve hours.

12. A device according to claim 1, wherein the chemonucleolysis agent comprises a nutrient component and a lubricant component, the nutrient component comprising chondroitin sulfate, glucosamine, or a combination thereof, and the lubricant component comprises lubricin, polyethylene glycol, or a combination thereof.

* * * * *